United States Patent
Fekete et al.

(10) Patent No.: US 10,694,724 B2
(45) Date of Patent: Jun. 30, 2020

(54) TRANSGENIC MOUSE FOR THE ASSESSMENT OF THYROID HORMONE (TH) ACTION

(71) Applicant: MAGYAR TUDOMÁNYOS AKADÉMIA KÍSÉRLETI ORVOSTUDOMÁNYI KUTATÓ INTÉZET, Budapest (HU)

(72) Inventors: Csaba Fekete, Budapest (HU); Balázs Gereben, Budapest (HU); Petra Mohácsik, Budapest (HU); Ferenc Erdélyi, Budapest (HU); Gábor Szabó, Budapest (HU)

(73) Assignee: Kisérleti Orvostudoányi Kutatóintézet, Budapest (HU)

( * ) Notice: Subject to any disclaimer, the term of this patent is extended or adjusted under 35 U.S.C. 154(b) by 25 days.

(21) Appl. No.: 15/531,100

(22) PCT Filed: Nov. 30, 2015

(86) PCT No.: PCT/HU2015/050020
§ 371 (c)(1),
(2) Date: May 26, 2017

(87) PCT Pub. No.: WO2016/083856
PCT Pub. Date: Jun. 2, 2016

(65) Prior Publication Data
US 2017/0325429 A1   Nov. 16, 2017

(30) Foreign Application Priority Data

Nov. 28, 2014 (HU) ..................... 1400563

(51) Int. Cl.
*A01K 67/027* (2006.01)
*C12N 15/00* (2006.01)
*C12N 15/63* (2006.01)
*C07H 21/04* (2006.01)
*C12N 15/85* (2006.01)
*A61K 49/00* (2006.01)
*C12Q 1/6897* (2018.01)
*G01N 33/50* (2006.01)
*G01N 33/78* (2006.01)

(52) U.S. Cl.
CPC ...... *A01K 67/0275* (2013.01); *A61K 49/0008* (2013.01); *C12N 15/85* (2013.01); *C12N 15/8509* (2013.01); *C12Q 1/6897* (2013.01); *G01N 33/5088* (2013.01); *G01N 33/78* (2013.01); *A01K 2217/052* (2013.01); *A01K 2217/07* (2013.01); *A01K 2217/20* (2013.01); *A01K 2217/203* (2013.01); *A01K 2227/105* (2013.01); *A01K 2267/0393* (2013.01); *C07H 21/04* (2013.01); *C12N 2015/859* (2013.01); *C12N 2800/90* (2013.01); *C12N 2830/002* (2013.01)

(58) Field of Classification Search
CPC .......... A01K 67/0275; A01K 2217/052; A01K 2227/105; C12N 15/63; C12N 15/85; C07H 21/04
USPC ......... 800/18, 25; 435/320.1; 536/23.2, 24.1
See application file for complete search history.

(56) References Cited

U.S. PATENT DOCUMENTS

2011/0265192 A1   10/2011   Bolund et al.
2012/0255041 A1   10/2012   Dressler et al.

FOREIGN PATENT DOCUMENTS

EP   1 365 034 A2   11/2003

OTHER PUBLICATIONS

Maggi et al., 2011, US 20110203008 A1.*
Carstea et al., 2009, World Journals of Stem Cells, vol. 1, No. 1, p. 22-29.*
Patil et al., 2011, Indian Journal of Public Health research & Development, vol. 2, No. 1, p. 106-109.*
Devoy et al., 2012, Nature Reviews Genetics, vol. 13, p. 14-20.*
Maksinnenko et al., 2013, Acta Naturae, vol. 5, No. 1, p. 33-46.*
Xuan et al., 2003, US 20030110522 A1.*
Khodarovich et al., 2013, Applied Biochemistry and Microbiology, vol. 49, No. 9, pp. 711-722.*
Moisyadi et al., 2011, US 20110130444 A1.*
Nucera et al.: "Maternal thyroid hormones are transcriptionally active during embryo-foetal development: results from a novel transgenic mouse model", Journal of Cellular and Molecular Medicine, 2009, vol. 14, No. 10, pp. 2417-2435.
Quignodon et al.: "Thyroid hormone signaling is highly heterogeneous during pre- and postnatal brain development", Journal of molecular endocrinology, 2004, vol. 33, pp. 467-476.
Ciana et al.: "Engineering of a Mouse for the in Vivo Profiling of Estrogen Receptor Activity", Molecular Endocrinology, 2001, vol. 15(7), pp. 1104-1113.
Mohácsik et al.: "A Transgenic Mouse Model for Detection of Tissue-Specific Thyroid Hormone Action", Endocrinology, 2018, vol. 159(2), pp. 1159-1171.

* cited by examiner

Primary Examiner — Shin Lin Chen
(74) Attorney, Agent, or Firm — Jason D. Voight

(57) ABSTRACT

A transgenic animal model that is suitable for the cell or tissue specific assessing of thyroid hormone (TH) action in vivo is described. The recombinant DNA construct and methods suitable to generate such an animal are also provided. The assessment of TH action is based on a reporter that is dependent on an endogenously expressed thyroid hormone receptor (TR) and coregulators of said receptor.

15 Claims, 11 Drawing Sheets

A

B

C

A

Ctrl

B

Cold

TRANSGENIC MOUSE FOR THE ASSESSMENT OF THYROID HORMONE (TH) ACTION

This is the national stage of International Application PCT/HU2015/050020, filed Nov. 30, 2015.

FIELD OF THE INVENTION

The invention relates to the field of cell or tissue specific assessing of thyroid hormone (TH) action in vivo and in vitro. A thyroid hormone action indicator animal model that allows assessing in vivo cell or tissue specific thyroid hormone action is provided together with the thyroid hormone action indicator transgenic recombinant DNA construct (THAIC) suitable to generate such a transgenic model animal.

BACKGROUND OF THE INVENTION

Thyroid hormone (TH) is a key regulator of a wide range of biological processes. Thyroid hormone exerts its effect on a broad range of crucial phenomena including cell proliferation, energy homeostasis, brain development and function. It is necessary for normal growth in children and young animals, as evidenced by the growth-retardation observed in thyroid deficiency. TH increases heart rate, cardiac contractility and cardiac output. It also promotes vasodilation, which leads to enhanced blood flow to many organs.

Both decreased and increased concentrations of thyroid hormone lead to alterations in mental state.

Normal reproductive behavior and physiology is dependent on having essentially normal levels of thyroid hormone. Hypothyroidism in particular is commonly associated with infertility.

Increased thyroid hormone levels stimulate fat mobilization, leading to increased concentrations of fatty acids in the plasma. Thyroid hormones stimulate almost all aspects of carbohydrate metabolism, including enhancement of insulin-dependent entry of glucose into cells and increased gluconeogenesis and glycogenolysis to generate free glucose.

The human thyroid gland secrets predominantly a stable prohormone, T4, that needs to be converted to T3 to initiate its nuclear receptor mediated biological effects (1). Thyroid hormone levels are relatively stable in the plasma, but intracellular TH concentration undergoes turbulent and tightly controlled changes evoked by specific physiological or pathophysiological stimuli. Thus TH action on the nuclear receptors is evoked by cell and tissue specific processes. The cell and tissue specific action of thyroid hormones is governed by local thyroid hormone metabolizing enzymes, transporter molecules, receptors and co-regulators (2-5). The cell type specific action of thyroid hormones is regulated by thyroid hormone transporters, deiodinase enzymes, thyroid hormone receptors and co-regulators relatively independently from the circulating thyroid hormone levels.

Receptors for thyroid hormones (TR) are nuclear DNA-binding proteins that function as hormone-responsive ligand-induced transcription factors. To date, the receptor subtypes TRα and TRβ with several isoforms have been identified. Both TRα and TRβ can bind the same thyroid hormone responsive element (TRE) located in the regulatory regions of thyroid hormone responsive genes (6). The typical consensus TRE half site is AGGTCA spaced by 4 nucleotides followed by the second AGGTCA half site (TRE DR-4) (7). Less typical TREs are represented by inverted palindromic or palindromic half sites (e.g. F2 or Pal) (7).

TRα plays major role in the regulation of heart rate and muscle whereas TRβ modulates serum cholesterol levels via actions in liver and feedback inhibition of TH production through the hypothalamic-pituitary-thyroid axis. TRs also exhibit subtype-specific effects in regulation of basal metabolic rate, bone development and other processes (6).

Treatment of patients with thyroid hormone would be beneficial for various symptoms e.g. obesity and hypercholesterolaemia. However, this treatment cannot be performed due to unfavorable, e.g. cardiac effects of thyroid hormone that results in tachycardia. Intense efforts are made to overcome this problem since obesity is getting a devastating health problem in Europe and the USA (8) by increasing the risk of type 2 diabetes, cardiovascular symptoms, oncogenesis and depression. In the USA, more than 65% of the population is overweight, 31% (more than 61 million people) is obese (www.obesityresearch.nih.gov) and the consequent direct and indirect costs exceed 100 billion USD (9). 20% of the population is obese (BMI>30 kg/m2) and additional 42% is overweight (BMI between 25-30 kg/m2) in Hungary (10). Furthermore, hypercholesterolaemia represents a massive health risk worldwide since it increases the risk for coronary heart diseases in large populations (~42% of men and 34% of women are diagnosed with hypercholesterolaemia in the USA) (11). It is a subject of intense R&D activity to generate TR isoform and/or tissue specific compounds that could modulate TH action in specific tissues while leaving it intact in others in order to exert the beneficial effects of thyroid hormone without evoking unwanted, e.g. cardiac symptoms.

Numerous studies have been set out to examine the effects of thyroid hormones and thyroid hormone analogues as well as to identify the role of the different TR subtypes and gene specific variations in transcriptional responses of different tissues to TH.

Lin et al. examined the gene specific actions of thyroid hormone receptor subtypes using genetically modified HepG2 and HeLa cells by introducing exogenous TRs into the cells (6).

EP 1 365 034 describes a promoter assay suitable for the assessment of thyroid hormone gene transcription. HepG2 cells were transformed with a 2×IROluc vector, carrying a TRE of two 12 bp inverted palindromes separated by an 8 bp spacer in front of a thymidine kinase minimal promoter and the luciferase gene. The construction is suitable for the determination of TH action in vitro in cell lines such as the HepG2 cells but does not allow the in vivo assessment of TH action since the recombinant construct is not functional in a transgenic animal.

Quignodon et al. report the construction of a transgenic reporter mouse to analyze the spatio-temporal distribution of thyroid hormone signaling during mouse brain development (12). The reporter system is utilizing a chimeric yeast Gal4DNA-binding domain—THα ligand-binding domain fusion protein to drive lacZ expression. The authors were able to generate two transgenic lines, called FINDT3A and FINDT3B, differing in the transgene integration site and copy number. The FINDT3 transgenic reporter system proved to be highly responsive to thyroid hormone in neuronal cells. Transgene expression was dependent on T3, however, the system worked independently of endogenous TR. Therefore this model is inappropriate to report on any regulation dependent on endogenously expressed thyroid hormone receptors.

Quignodon et al. also recognized that interactions occurring in the N-terminal domains of TR and variations in TR isoforms expression might generate another level of regulation not detected by the FINDT3 system. This renders the model unsuitable to test the effects of isoform specific TH analogues and antagonists. The authors also considered it possible that the onset of endogenous T3 signaling might occur slightly earlier than detected by the model system, because the accumulation of β-galactosidase in a self-inducible system could be delayed as the chimeric receptor used for the generation of the recombinant DNA construct self-regulates its own expression. Therefore, the use of the model is limited when performing time-curve studies in live animals.

Nucera et al. have generated a transgenic mouse model expressing the LacZ reporter gene (encoding β-galactosidase) under a TRE, to specifically trace maternal TH transcription activity during early and late embryo-foetal development. Although the authors could successfully assess TH action with the model at embryonic stages, information on adult animals is missing. This might be due to the complexity of the regulation of both transgene expression and TH related gene regulation in adult animals which often results in non-functional (e.g. silenced) recombinant constructs in adults. Also, the 2×TRE β gal model does not allow detection in live animals (13)

There is apparently a need for complex and reliable in vivo and in vitro models for the assessment of thyroid hormone action as well as for the assessment of TR agonists or antagonists, modulators of co-regulators or thyroid hormone transporters produced by the pharmaceutical industry to take advantage of the beneficial effects of TH action (e.g. weight loss, lowered cholesterol level) without evoking hazardous side effects of TH (e.g. lipogenesis and tachycardia). Discovery-driven scientific studies would also greatly benefit from a model that allows better understanding of cell-type specific thyroid hormone action to decipher underlying mechanism of the regulation of cell proliferation, energy homeostasis and any other symptom/condition associated with altered thyroid hormone economy (e.g. nonthyroidal illness syndrome, testing of thyroid hormone combination therapy).

BRIEF DESCRIPTION OF THE INVENTION

The invention relates to a transgenic animal that allows assessing thyroid hormone (TH) action in vivo. The transgenic mammal of the invention is suitable for the tissue specific and/or cell type specific measurement of TH mediated regulation of gene transcription and is dependent on the endogenous apparatus of TH action, including different isoforms of TH receptor (TR) subtypes and coregulators of the TH receptors. In a particular embodiment the expression of a reporter protein or its encoding mRNA is used as readout. The transgenic animal of the invention allows the assessment of thyroid hormone (TH) action if TR is present or even a lack of such action if either TR or TH is not present. The transgenic animal of the invention also allows the assessment of the level of tissue and/or cell type specific thyroid hormone (TH) action in cells and/or tissues expressing any isoform of any endogenously expressed TR subtype.

According to one aspect, the invention relates to a thyroid hormone action indicator transgenic mammalian animal comprising cells having stably integrated in their genome a recombinant DNA construct useful for the assessment of thyroid hormone (TH) action, wherein the recombinant DNA construct comprises, in 5' to 3' direction, at least the following elements:
a thyroid hormone responsive segment, comprising one or more thyroid hormone responsive element (TRE),
a promoter operably linked to an expression enhancer,
a coding sequence encoding a reporter.

In this embodiment the promoter drives expression of the reporter in cells of one or more tissue(s) of said animal.

The thyroid hormone receptor (TR) is expressed independently from the construct, when it is expressed in said cells, i.e. in the same cells in which the recombinant DNA construct is present and operable. Alternatively, the TR is not expressed in said cells.

In particular said recombinant DNA construct is free of a sequence encoding a thyroid hormone receptor.

A TR, if present and a TH, if present, forms a complex (TR-TH complex) in said cells; this complex, if present, up-regulates expression of the reporter via the thyroid hormone responsive segment, whereby the level of the expression of the reporter correlates, preferably positively correlates, with the level of said complex.

Thereby regulation of the reporter is dependent on a thyroid hormone receptor (TR). The regulation of the reporter can be dependent also on coregulators of said receptor. The regulation of the reporter is dependent on a thyroid hormone receptor which is in the presence of TH binding, acts as a TRE-dependent activator, while in the absence of TH binding, acts as a TRE-dependent repressor and thereby mediates the transcriptional effects of thyroid hormone via the thyroid hormone responsive segment.

In particular, when a complex comprising the TR and TH is formed in the cell comprising the recombinant DNA construct, said complex activates the promoter and thereby transcription of the coding sequence encoding the reporter. The level of activation and/or the transcription depends on and/or correlates with the level of the liganded TR complex.

The complex of the TR and the TH is an activator.

Thus, the TRE can be activated by binding of said complex.

If desired the TR and/or the complex of the TR and the TH is bound to one or more further protein which are present in the cells comprising the construct and which are coregulators of TH action.

In an embodiment the thyroid hormone responsive segment of the recombinant DNA construct integrated in the genome of the animal of the invention shows TR-dependent responsiveness or sensitivity to triiodothyronine (T3).

In an embodiment the thyroid hormone responsive segment contains a thyroid hormone responsive element (TRE) that activates gene transcription and/or expression when TR is liganded with TH.

The TRE that binds an unliganded TR may act as a repressor of gene transcription and/or expression.

In another embodiment the thyroid hormone responsive segment of the recombinant DNA construct integrated in the genome of the animal of the invention comprises a single copy or multiple copies of a thyroid hormone responsive element.

In a preferred embodiment the TRE is the thyroid hormone response element of the dio1 gene, more preferably the human dio1 gene.

In a highly preferred embodiment the TRE is a thyroid hormone response element (TRE) having the sequence motif of GGGTCA nnnn AGGTCA, highly preferably the TRE of the 5' flanking region of the human dio1 gene having the sequence of GGGTCA tctg AGGTCA (14).

In yet another embodiment the TRE is present in more than one copy, preferably in 1, 2, 3, 4 or 5 copies, highly preferably in 3 copies, in particular, 3 copies of the TRE of the dio1 gene.

In an embodiment the promoter is a ubiquitous promoter.

In a preferred embodiment the promoter is a minimal promoter with minimal/lacking responsiveness to transcription factors beyond those that are required to form the basic transcriptional complex.

In a preferred embodiment the promoter is the thymidine kinase (TK) minimal promoter.

In a highly preferred embodiment the promoter is the thymidine kinase (TK) minimal promoter of the Herpes simplex virus.

In a preferred embodiment the expression enhancer contains intronic sequences.

In a highly preferred embodiment the expression enhancer is in the form of an expression enhancer cassette preferably containing an untranslated leader sequence, more preferably an untranslated leader sequence of a beta globin gene intron sequence, highly preferably the untranslated leader (exon 1)-HTLV-1 R-Synthetic Rabbit β-globin-based 3' intron-intron unit of the NTC8681 vector.

In another embodiment the reporter encoded by the coding sequence encoding a reporter is a protein which, when expressed in a cell, said cell provides an optically detectable signal, the optically detectable signal being preferably visible light.

In certain embodiments the protein is an enzyme the activity of which results in a light emitting substrate, highly preferably a luciferase; or a colored substrate, e.g. lacZ.

In other embodiments said protein is a fluorescent protein, preferably selected from GFP, RFP, YFP, CFP, tdTomato.

In a highly preferred embodiment the coding sequence for the reporter protein is a codon optimized and/or methylation resistant sequence, preferably a dCpG sequence, highly preferably a dCpG Luciferase coding region.

In yet another embodiment the reporter encoded by the coding sequence encoding a reporter is a protein the amount and/or activity of which, when expressed in a cell, can be measured by enzymatic assays.

In another embodiment the recombinant DNA construct further comprises a sequence coding for a resistance marker.

In yet another embodiment the sequences coding for the reporter and the resistance marker are fused to each other in frame; wherein the recombinant DNA construct also comprises a polyadenylation segment downstream from the coding sequences.

In certain embodiments the resistance marker is an antibiotic resistance marker, preferably encoded in an antibiotic resistance cassette which is highly preferably a zeocin resistance cassette, in particular a ShBle zeocin resistance cassette.

In yet another embodiment the recombinant DNA construct is flanked by insulator sequences to protect the DNA construct from influences from neighbouring genome sequences.

In a highly preferred embodiment the DNA construct is assembled in a pWHERE vector and/or is flanked by the H19 insulators in particular of that of the vector.

The recombinant DNA construct according to the invention may be assembled in any suitable vector that can be grown in *E. coli* (e.g. pGemT, pUC, pCI-neo, pGL3-basic, pSPORT, pEYFP, D10).

In an embodiment the recombinant DNA construct is integrated into the genome of the animal of the invention by a transposon based delivery.

Highly preferably as a transposon based delivery system the Sleeping Beauty system is applied.

In a preferred embodiment the animal of the invention is a mammal, preferably a rodent, preferably a murine animal.

In this embodiment the mammalian animal is highly preferably a mouse.

In a highly preferred embodiment the transgenic animal of the invention is a mouse comprising stably integrated in its genome a recombinant DNA construct useful for the assessment of thyroid hormone action, wherein the recombinant DNA construct comprises, in 5' to 3' direction, the following elements a thyroid hormone responsive segment, preferably containing one or more TRE(s) having the sequence motif of GGGTCA nnnn AGGTCA, preferably the TRE of the 5' flanking region of a dio1 gene, preferably of the human dio1 gene, a promoter operably linked to an expression enhancer, wherein the promoter is preferably a thymidine kinase minimal promoter, preferably the thymidine kinase minimal promoter of the Herpes simplex virus, the expression enhancer is preferably in the form of an expression enhancer cassette preferably containing an intronic sequence e.g. an intron-intron unit and an untranslated leader sequence, in particular the untranslated leader (exon 1)-HTLV-1 R-Synthetic Rabbit β-globin-based 3' intron-intron unit of the NTC8681 vector, a coding sequence encoding a reporter, wherein the coding sequence is preferably a dCpG Luciferase coding region, wherein said elements are flanked by insulator sequences, preferably by H19 insulators.

In an embodiment the recombinant DNA construct is integrated into the genome of the animal of the invention by the Sleeping Beauty transposon system.

In an embodiment the animal is heterozygous for the DNA construct.

In an embodiment the animal comprises multiple copies of the DNA construct in its genome.

In yet another embodiment the animal preferably comprises a single copy of the DNA construct in its (each) haploid genome(s).

According to another aspect, the invention relates to a recombinant DNA construct that allows assessing thyroid hormone action.

The recombinant construct according to the invention comprises the following elements: a thyroid responsive segment that is responsive to thyroid hormone dependent action via thyroid hormone receptors, a minimal promoter with tissue independent, ubiquitous expression in mammalian tissues with minimal/lacking responsiveness to transcription factors beyond those that are required to form the basic transcriptional complex; a coding region encoding a reporter gene the amount of which can be sensitively detected in vivo in live animals, ex vivo in tissue samples and/or in vitro in cultured cells; an expression enhancer cassette to promote the activity of the minimal promoter driven transcriptional unit; insulators that isolate the thyroid hormone responsive transgenic cassette from the neighboring chromosomal regions.

In an embodiment the recombinant DNA construct of the invention comprises, in 5' to 3' direction, at least the following elements:

a thyroid hormone responsive segment, a promoter operably linked to an expression enhancer, a coding sequence encoding a reporter and the regulation of the reporter is dependent on endogenously expressed thyroid hormone receptors and coregulators mediating the transcriptional effects of thyroid hormone via the thyroid hormone responsive segment.

In this embodiment the promoter is capable of driving expression of the reporter in cells of one or more tissue(s) of said animal. Preferably the promoter is a ubiquitous promoter.

A sequence coding a thyroid hormone receptor (TR) is not part of the construct i.e. said recombinant DNA construct is free of a sequence encoding a TR. Thus a TR, if any, is expressed independently from the construct, when it is expressed in said cells, i.e. in the same cells in which the recombinant DNA construct is present and operable. Alternatively, the TR is not expressed in said cells.

A TR, if present and a TH, if present, forms a complex (TR-TH complex) in said cells; this complex, if present, up-regulates expression of the reporter via the thyroid hormone responsive segment, whereby the level of the expression of the reporter correlates, preferably positively correlates, with the level of said complex. In one embodiment the thyroid hormone responsive segment of the recombinant DNA construct of the invention shows TR-dependent responsiveness or sensitivity to T3.

In one embodiment the thyroid hormone responsive segment contains a thyroid hormone responsive element that activates gene expression when TR is liganded with TH.

In another embodiment the thyroid hormone responsive segment of the recombinant DNA construct of the invention comprises a single copy or multiple copies of a thyroid hormone responsive element.

In a preferred embodiment the TRE is the thyroid hormone response element of the dio1 gene, more preferably the human dio1 gene.

In a highly preferred embodiment the TRE is a thyroid hormone response element (TRE) having the sequence motif of GGGTCA nnnn AGGTCA, highly preferably the TRE of the 5' flanking region of the human dio1 gene having the sequence of GGGTCA tctg AGGTCA.

In yet another embodiment the TRE is present in one or more than one copy, preferably in 1 to 5 copies, preferably in 3 copies.

In an embodiment the promoter in the recombinant DNA construct of the invention is a ubiquitous promoter.

In a preferred embodiment the promoter is a minimal promoter with minimal/lacking responsiveness to transcription factors beyond those that are required to form the basic transcriptional complex.

In a preferred embodiment the promoter is the thymidine kinase minimal promoter.

In a highly preferred embodiment the promoter is the thymidine kinase minimal promoter of the Herpes simplex virus.

In a preferred embodiment the expression enhancer contains intronic sequences.

In a highly preferred embodiment the expression enhancer in the recombinant DNA construct according to the invention is in the form of an expression enhancer cassette preferably containing an untranslated leader sequence, more preferably an untranslated leader sequence of a beta globin gene intron sequence, highly preferably the untranslated leader (exon 1)-HTLV-1 R-Synthetic Rabbit β-globin-based 3' intron-intron unit of the NTC8681 vector.

In another embodiment the reporter encoded by the coding sequence encoding a reporter is a protein which, when expressed in a cell, said cell provides an optically detectable signal, the optically detectable signal being preferably visible light.

In certain embodiments the protein is an enzyme the activity of which results in a light emitting substrate, highly preferably a luciferase; or a colored substrate, e.g. lacZ.

In other embodiments said protein is a fluorescent protein, preferably selected from GFP, RFP, YFP, CFP, tdTomato.

In a highly preferred embodiment the coding sequence for the reporter protein is a codon optimized and/or methylation resistant sequence, preferably a dCpG sequence, highly preferably a dCpG Luciferase coding region.

In yet another embodiment the reporter encoded by the coding sequence is a protein the amount and/or activity of which, when expressed in a cell can be measured by enzymatic assays.

In another embodiment the recombinant DNA construct of the invention further comprises a sequence coding for a resistance marker.

In yet another embodiment the sequences coding for the reporter and the resistance marker are fused to each other in frame; wherein the recombinant DNA construct also comprises a polyadenylation segment downstream from the coding sequences.

In certain embodiments the resistance marker is an antibiotic resistance marker, preferably encoded in an antibiotic resistance cassette which is highly preferably a zeocin resistance cassette, in particular a ShBle zeocin resistance cassette.

In yet another embodiment the recombinant DNA construct is flanked by insulator sequences to protect the DNA construct from influences from neighboring sequences.

In a highly preferred embodiment the DNA construct is assembled in a pWHERE vector and is flanked by the H19 insulators in particular of that of the vector.

The recombinant DNA construct of the invention may be assembled in any suitable vector, e.g that can be grown in *E. coli* (e.g. pGemT, pUC, pCI-neo, pGL3-basic, pSPORT, pEYFP, D10).

In a highly preferred embodiment a recombinant DNA construct useful for the assessment of thyroid hormone action is provided, wherein the recombinant DNA construct comprises, in 5' to 3' direction, the following elements a thyroid hormone responsive segment, preferably containing one or more TRE having the sequence motif of GGGTCA nnnn AGGTCA, preferably the TRE of the 5' flanking region OF a dio1 gene, preferably of the human dio1 gene, a promoter operably linked to an expression enhancer, wherein the promoter is preferably a thymidine kinase minimal promoter, preferably the thymidine kinase minimal promoter of the Herpes simplex virus, the expression enhancer is preferably in the form of an expression enhancer cassette preferably containing an intronic sequence e.g. an intron-intron unit and an untranslated leader sequence, in particular the untranslated leader (exon 1)-HTLV-1 R-Synthetic Rabbit β-globin-based 3' intron-intron unit of the NTC8681 vector, a coding sequence encoding a reporter, wherein the coding sequence is preferably a dCpG Luciferase coding region, wherein said elements are flanked by insulator sequences, preferably by H19 insulators.

In yet another aspect of the invention a targeting expression vector useful to integrate the recombinant DNA construct into the genome of said transgenic animal is provided wherein said targeting construct contains the recombinant DNA construct of the invention between transposase recognition sequences.

In an embodiment the transposase recognition sequences are ITR transposase recognition sequences.

In this embodiment the transposon system is highly preferably the Sleeping Beauty transposon system.

In another aspect of the invention a cell of an animal comprising the DNA construct of the invention is provided wherein said cell expresses increased levels of the reporter protein in the presence of said TH.

In yet another embodiment the cell is a cell derived from said transgenic animal.

In an embodiment said cell is a cell being transformed with a DNA construct defined above.

In another embodiment the cell is of a cell line, preferably an established cell line not derived from the animal of the invention.

In another aspect of the invention a method of producing the transgenic animal of the invention is provided.

In an embodiment the method of producing the transgenic animal of the invention comprises the following steps:
  introduction of the recombinant DNA targeting construct of the invention into the pronucleus of fertilized oocytes,
  identification of the founder animals,
  crossing the founders with wild type animals,
  inbred coupling of the F1 generation.

In another embodiment the method of producing the transgenic animal of the invention may comprise any genetic engineering method suitable to produce a transgenic animal containing the recombinant DNA construct of the invention, e. g. DNA microinjection, stem cell mediated gene transfer, knock-in techniques, etc.

In a specific embodiment the method of producing the transgenic animal of the invention comprises the following steps
  injecting the pronucleus of fertilized oocytes with a mixture containing the plasmid harbouring the targeting cassette and the in vitro transcribed mRNA encoding the Sleeping beauty transposon,
  identification of the founders using TaqMan assay with a Luciferase probe.

In another aspect of the invention a method of transforming a cell with the recombinant DNA construct of the invention is provided wherein the method comprises the steps of introducing the recombinant DNA construct into the cell and culturing said cell.

According to another aspect, the invention provides a use of the transgenic animal according to the invention for the assessment or monitoring tissue and/or cell type specific TH action in vivo.

The use of a cell, tissue or organ derived from the transgenic animal according to the invention for the assessment of tissue and/or cell type specific TH action ex vivo is provided.

The use of a cell or a cell line transformed with the recombinant DNA construct of the invention and/or derived from the transgenic animal of the invention for the assessment or monitoring of TH action in said cell in vitro is also provided.

The use of the transgenic animal of the invention and/or the use of a cell, tissue or organ of said animal and/or the use of a cell or a cell line comprising the DNA construct of the invention for the assessment or monitoring the action of thyroid receptor agonists or antagonists, modulators of coregulators or thyroid hormone transporters is provided.

According to another aspect a method for assessing or monitoring in vivo TH action is provided, said method comprising
  providing a transgenic animal defined above or in the claims or a transgenic animal comprising the recombinant DNA construct defined above or in the claims,
  modulating thyroid hormone action in the transgenic animal,
  detecting the level of the expression of the reporter in cells of one or more tissue(s) live or in tissue samples of said animal,
wherein the level of the expression of the reporter correlates with TH action in said cells of one or more tissue(s).

A method for assessing or monitoring ex vivo TH action, said method comprising
  providing a cell, tissue or organ derived from a transgenic animal defined above or in the claims, which cell, tissue or organ comprises the recombinant construct as defined above or in the claims,
  modulating thyroid hormone action in said cell, tissue or organ,
  detecting the level of the expression of the reporter in said cell, tissue or organ,
wherein the level of the expression of the reporter correlates with TH action in said cell, tissue or organ.

A method for assessing or monitoring in vitro TH action, said method comprising
  providing a cell of a transgenic animal comprising the DNA construct as defined above or in any of the claims, which cell comprises the recombinant DNA construct as defined above or in the claims, or providing a cell being transformed with the recombinant construct defined above or in the claims,
  modulating thyroid hormone action in said cell,
  detecting the level of the expression of the reporter in said cell,
wherein the level of the expression of the reporter correlates with TH action in said cell.

A method for the assessment or monitoring the effect of an agent, a modulation or modification or a treatment on in vivo TH action, said method comprising
  providing a transgenic animal defined above or in the claims,
  administering said agent or applying said modulation or modification or treatment to said animal,
  detecting the level of the expression of the reporter in cells of one or more tissue(s) of said animal,
wherein the level of the expression of the reporter correlates with TH action in said cells of one or more tissue(s).

A method for the assessment or monitoring the effect of an agent, a modulation or modification or a treatment on ex vivo TH action, said method comprising
  providing a cell, tissue or organ derived from a transgenic animal defined above or in the claims,
  administering said agent or applying said modulation or modification or treatment to said cell, tissue or organ,
  detecting the level of the expression of the reporter in said cell, tissue or organ,
wherein the level of the expression of the reporter correlates with TH action in said cell, tissue or organ.

A method for the assessment or monitoring the effect of an agent, a modulation or modification or a treatment on in vitro TH action, said method comprising
  providing a cell of a transgenic animal comprising the DNA construct as defined above or in any of the claims, which cell comprises the recombinant DNA construct as defined above or in the claims, or providing a cell being transformed with the recombinant construct defined above or in the claims, administering said agent or applying said modulation or modification or treatment to said cell, detecting the level of the expression of the reporter in said cell, wherein the level of the expression of the reporter correlates with TH action in said cell.

The method for the assessment or monitoring the effect of an agent, a modulation or modification or a treatment on in vivo TH action, wherein said agent, modulation or modification or treatment is selected from thyroid receptor agonists and antagonists, modulators of coregulators and thyroid hormone transporters and metabolising enzymes.

The method for the assessment or monitoring the effect of an agent, a modulation or modification or a treatment on ex vivo TH action, wherein said agent, modulation or modification or treatment is selected from thyroid receptor agonists and antagonists, modulators of coregulators and TH transporters and metabolising enzymes.

The method for the assessment or monitoring the effect of an agent, a modulation or modification or a treatment on in vitro TH action, wherein said agent, modulation or modification or treatment is selected from thyroid receptor agonists and antagonists, modulators of coregulators and TH transporters and TH metabolising enzymes.

Thyroid hormone action may be modulated e.g. by the administration of a TR agonist, a TR antagonist, a modulator of a coregulator or a modulator of a TH transporter, a modulator of TH production, by modulation of TH transportation, by modulation of TH production, by modulation of TH metabolism, by modulation of TR expression or by genetic modulation of a TR gene. The method of the invention is suitable to detect the modulation of TH action irrespective of the source of said modulation and therefore suitable to identify new agents, treatments, mechanisms or pathways affecting TH action.

In an embodiment the method further comprises the detection of the expression level of thyroid hormone receptor (TR) in said cells, wherein the level of the expression of the reporter correlates with TR-mediated TH action in said cells of one or more tissue(s). According to this embodiment TR expression may be provided in said cells by an expression construct separate from the recombinant construct of the invention. When the expression level of thyroid hormone receptor is detected in the cells, the changes of the expression of the reporter may be indicative of a change in the expression or functioning of TR.

According to another aspect of the invention a mouse model of a TH action related disease or condition is provided, comprising a mouse comprising the recombinant DNA construct defined above and in the claims. In an embodiment the mouse further comprises a genetic modification or spontaneously generated changes in a gene associated with a TH action related disease.

In a preferred embodiment the genetic modification affects a gene selected from the group comprising TRα, TRβ and MCT8 (monocarboxylate transporter 8).

In another embodiment non-thyroidal illness is induced in the mouse of the mouse model of a TH action related disease or condition.

In still another embodiment obesity is induced in the mouse of the mouse model of a TH action related disease or condition.

In another embodiment the mouse of the mouse model of a TH action related disease or condition is an aged mouse.

Definitions

A "transgenic" animal is a genetically modified animal which comprises in its genome an expressible nucleic acid sequence which is different from animal nucleic acid sequences present in nature.

"Genetic modification" is a process in which the genetic material of a living organism has been altered in a way that does not occur naturally e. g. by recombination and/or recombination and mating.

The term "thyroid hormone" (TH) as used herein may refer to any form, proform, or derivative of the thyroid hormone, i.e. thyroid hormone as used herein may refer to the prohormone form of triiodothyronine, conventionally termed thyroxine or T4 and it may also refer to triiodothyronine (T3). Preferably, a TH as used herein refers to a thyroid hormone which, when is bound to and/or forms a complex with a thyroid hormone receptor (TR) acts or functions as an activator of the transcription of a gene regulated by a thyroid hormone responsive element. Still more preferably the thyroid hormone is 3,5,3'-triiodothyronine (T3). A "thyroid hormone response segment", "thyroid hormone responsive segment" or "TRE segment" as used herein is a nucleic acid segment where the nuclear receptors capable of binding thyroid hormone (i.e. thyroid hormone receptors) may bind thereby regulating the transcription of genes affected by thyroid hormone action. A thyroid hormone response segment may comprise one or more thyroid hormone response elements of one or more genes.

The term "thyroid hormone response element", thyroid hormone responsive element" or "TRE" describes a nucleic acid sequence where the nuclear receptors capable of binding thyroid hormone (i.e. thyroid hormone receptors) may bind to said sequence thereby regulating the transcription of genes affected by thyroid hormone action. The consensus TRE half site is AGGTCA spaced by 4 nucleotides followed by the second AGGTCA half site (TRE DR-4) (7). Less typical TREs are represented by inverted palindromic or palindromic half sites (e.g. F2 or Pal). The DR-4 is equally potent both for TRα and TRβ and binds the most typical form of liganded TR, the TR-RXR (Thyroid hormone receptor -Retinoid-X-Receptor) heterodimer. TRE as used herein refers to a nucleic acid sequence where a thyroid hormone receptor may bind to thereby positively regulating the transcription of genes affected by thyroid hormone action, i.e. the TRE is a "positive" TRE. On a TRE-containing target gene, TH binding acts as a switch between repressed and activated states if the TRE contained by said gene is a "positive" TRE. "Negative TRE"-s on the other hand, may mediate a negative regulatory effect of TH. The terms "positive" TRE and "negative TRE" may be understood as described in (15).

The term "5' flanking region of the human dio1 gene" refers to the genomic regulatory region of the human dio1 gene located 5' of the transcriptional start site.

A "promoter" is a DNA segment preceding the starting point of transcription where the RNA polymerase and transcription factors bind to initiate transcription; a promoter is capable of driving and regulating expression of a gene, e.g. a transgene in an organism.

A "minimal promoter" (or "native promoter") is a promoter having a sequence comprising elements required and sufficient to drive expression of a gene; preferably a minimal promoter lacks response elements and lacks enhancer elements, highly preferably lacks tissue-specific regulatory elements, even more preferably lacks or essentially lacks regulatory elements. Preferably, minimal promoters consist of a single fragment from the 5' region of a given gene and comprise a core promoter and its natural 5'UTR. In an embodiment the 5'UTR may contain an intron.

A "ubiquitous promoter" is a promoter which is active in a plurality of cells and tissues, preferably in a wide range of cells and tissues.

As used herein, the thymidine kinase (TK) minimal promoter is a portion of the TK promoter that is required and sufficient to run the transcription of a cassette cloned 3' to said promoter.

The thymidine kinase (TK) minimal promoter of the Herpes simplex virus (HSV) is a portion of the TK promoter derived from said virus, that is required and sufficient to run the transcription of a cassette cloned 3' to said promoter.

An "expression enhancer" or "expression enhancer element" is a DNA sequence that acts together with and/or is operably linked to a promoter and promotes, facilitates or enhances the level of the expression of a gene product that is under the control of said promoter.

The term "derived from" or "cell derived from" indicates the origin of the cell or object that is "derived from". The cell or object that is "derived from" is taken, received, obtained especially from a specified source or has its origin especially in a specified source. Thus the "cell derived from the transgenic animal" may indicate any cell prepared, obtained or taken from said animal as well as the cells obtained by culturing such a cell.

When the terms "one", "a", or "an" are used in this disclosure, they mean "at least one" or "one or more," unless otherwise indicated. The singular forms of nouns, such as "a TRE" may also cover the plural form of said noun.

Thyroid hormone action was assessed in three different time points after i.p. injection of 150 μg LPS, by real time PCR analysis of luciferase mRNA level in microdissected samples of ARC-ME region in line #23 THAIM mice. LPS evoked significant increase in luciferase mRNA level after 8 h (A), that was preceded with the elevation of D2 mRNA (B). In the PVN, TRH mRNA markedly decreased after 8 h, at the time point when thyroid hormone action reached the maximum in the ARC-ME (C).* p<0.05,p<0.01, * p<0.001; by one way ANOVA followed by Newman-Keuls post-hoc test. Data are shown as Mean±SEM (n=5).

Figure 7:
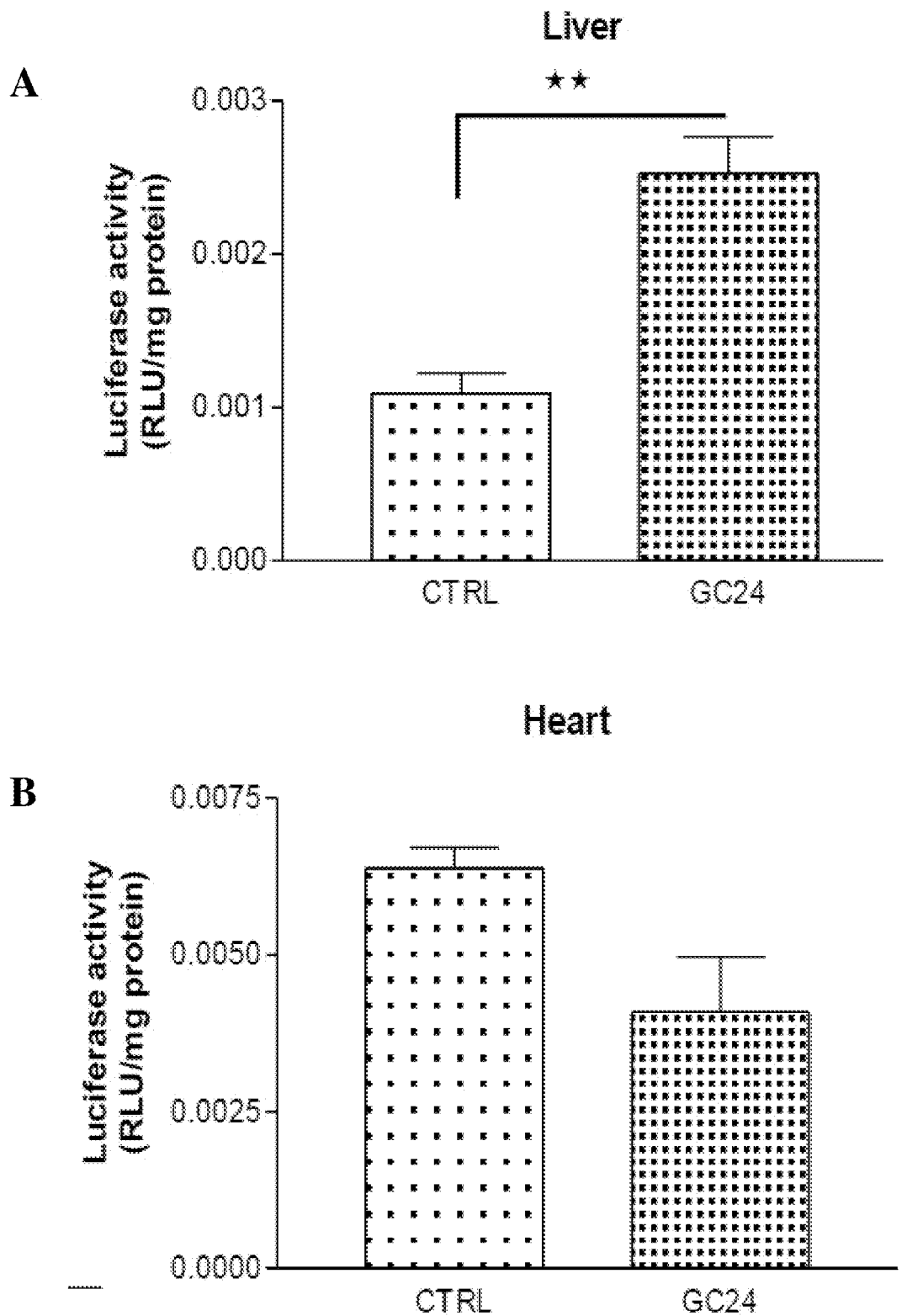

FIG. 7. The transgenic mouse model is capable to detect thyroid hormone receptor isoform specific T3 actions. The TRβ agonist GC-24 (i.p. 1.53 nM/g BW) significantly increased Luciferase activity in TRβ isoform dominant liver after 24 hours, while Luciferase activity did not change in TRα isoform dominant heart. Mean±SEM (n=5) ** p<0.01 by t test.

Figure 8:
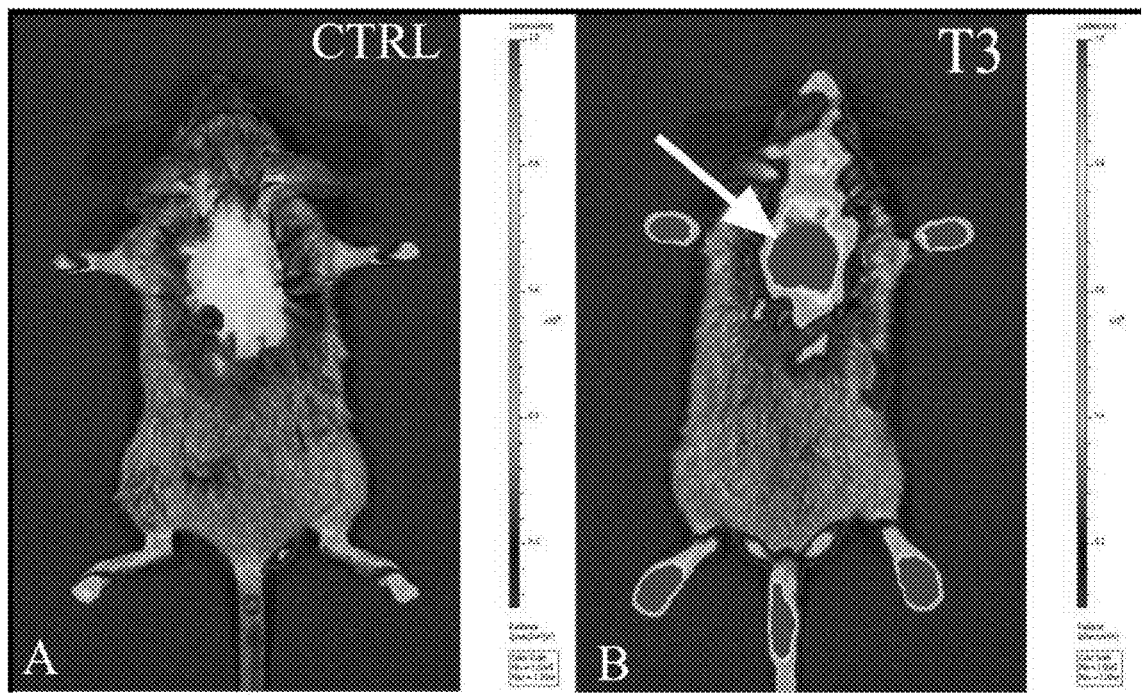
Figure 8:
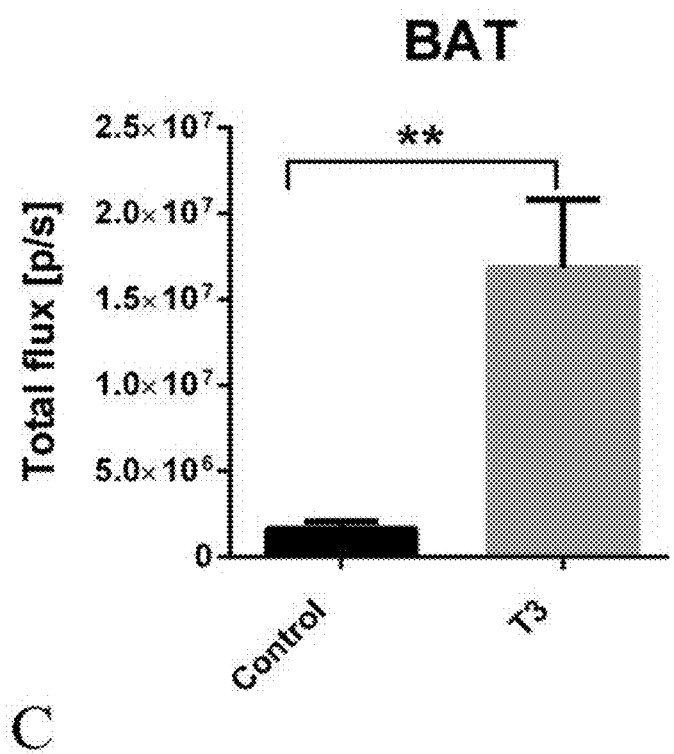
Figure 8:
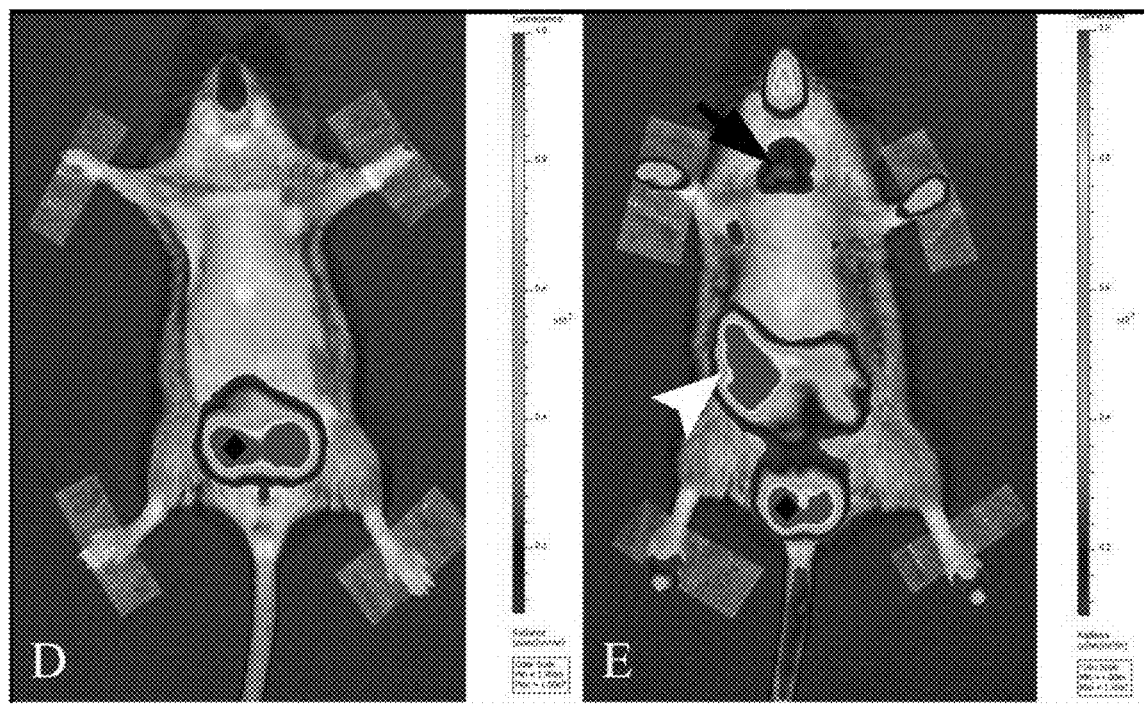
Figure 8:
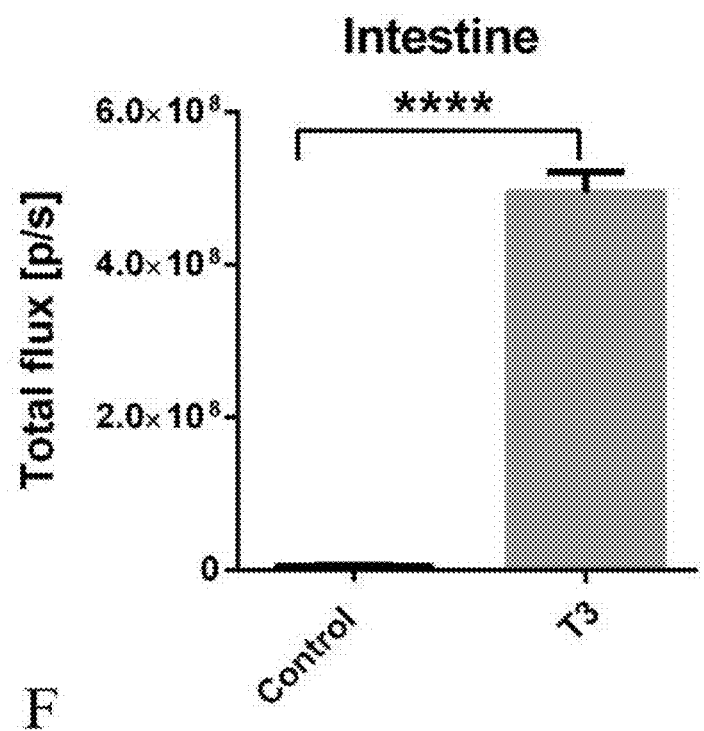

FIG. 8. The transgenic mouse model allows the detection of TH action in live animals In vivo bioluminescence imaging was performed to assess the role of T3 on iBAT and intestine of #4 THAIM mouse line following i.p. luciferin administration. Representative images of control (A,D) and T3 treated (B,E) mice. Light intensity diagram of iBAT and small intestine (C,F). Mean±SEM (n=4)  p<0.01 p<0.0001 by t test.

Figure 9:
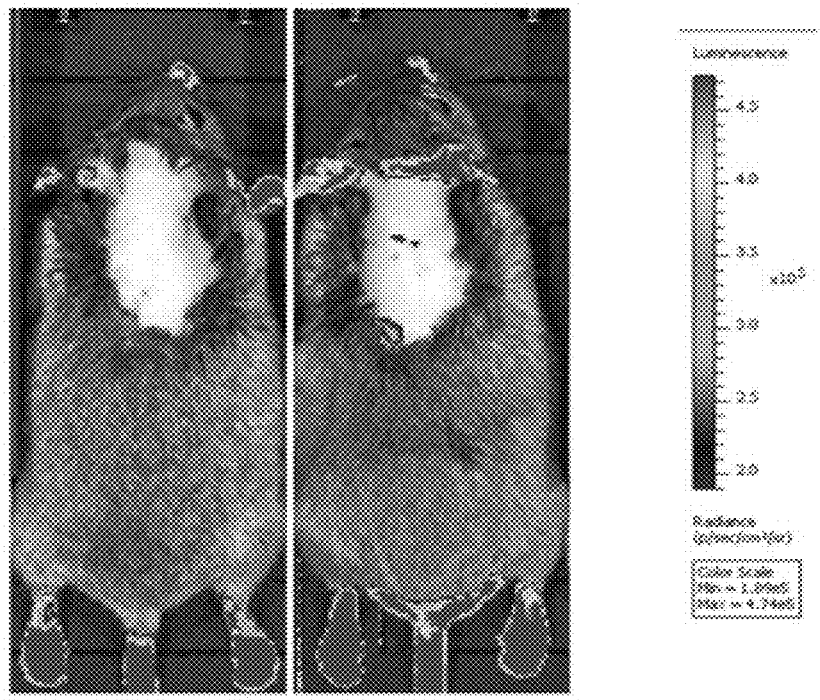
Figure 9:
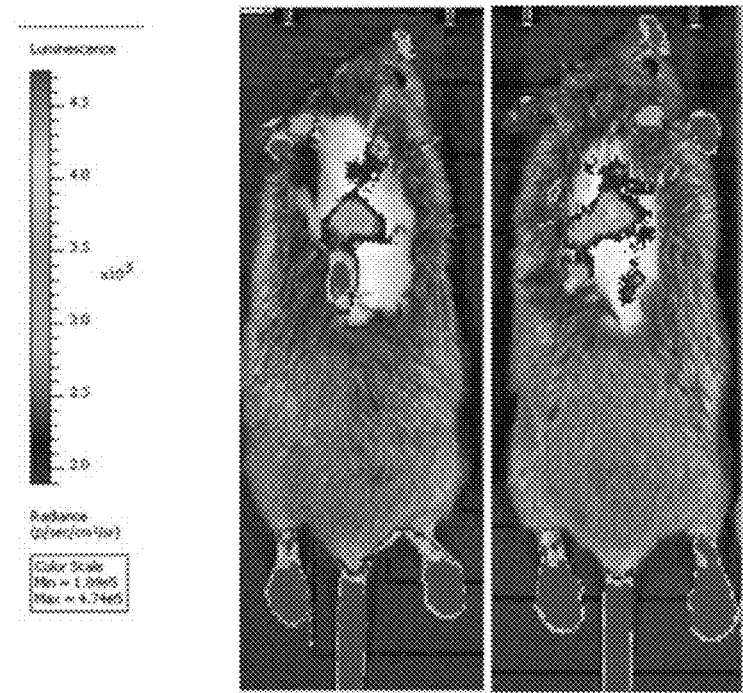
Figure 9:
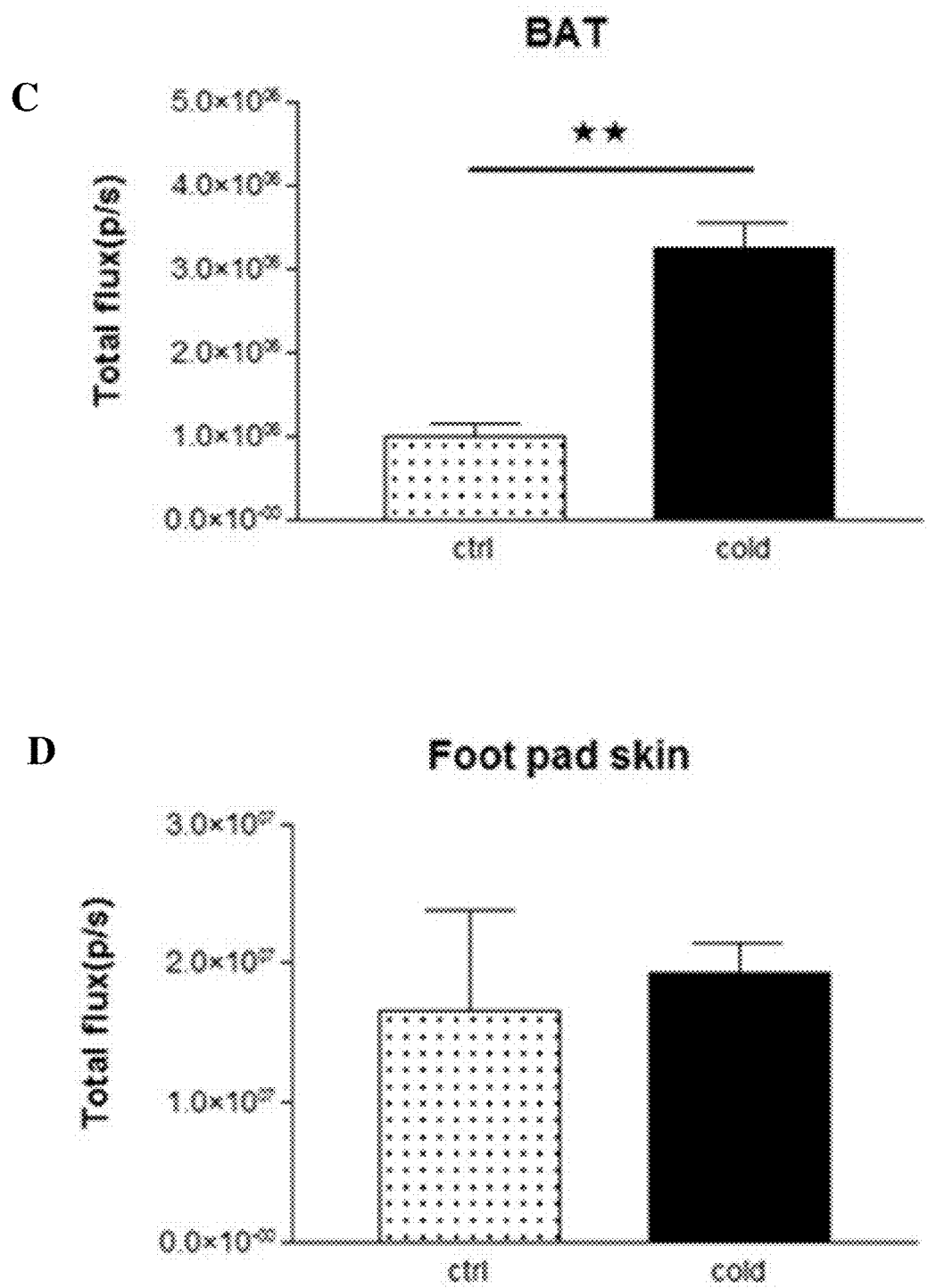

FIG. 9. THAIM allows detection of physiological stimulus induced changes of TH action in live animals In vivo bioluminescence imaging was performed to assess the role of 24 h cold stress on iBAT and skin of #4 THAIM mouse line following i.p. luciferin administration. Representative images of control (A) and cold stressed (B) mice. Light intensity diagram of iBAT and skin (C,D). Note that cold induced a significant increase of luciferase activity in the region of iBAT, while the luciferase activity was unchanged in other skin regions like the footpad. Mean±SEM (n=4) ** p<0.001 by t test.

Figure 10:
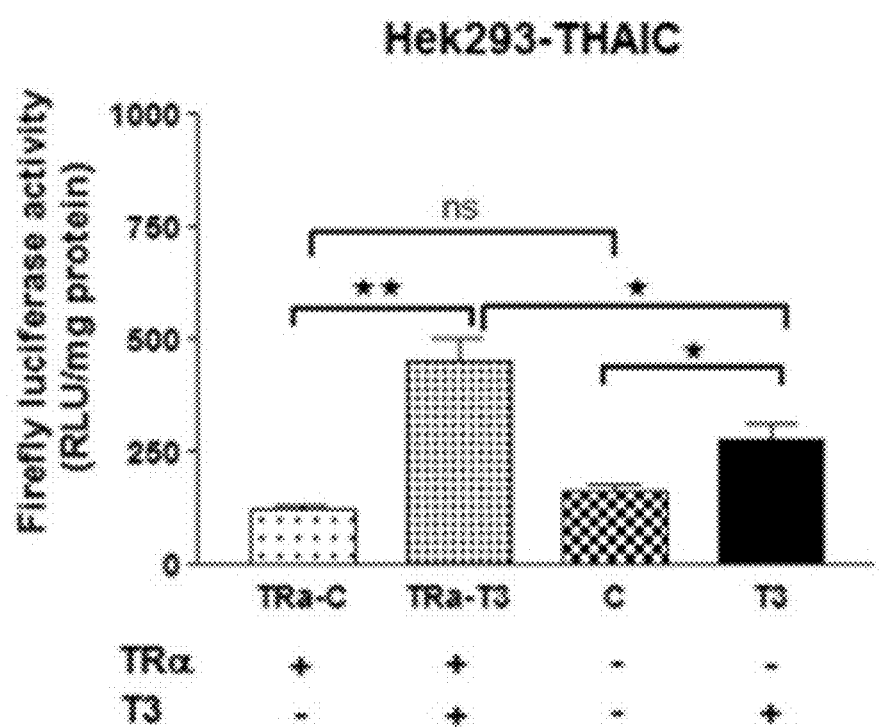

FIG. 10. The THAIC targeting construct is responsive to T3 in the HEK293 cell line The HEK293-THAIC cell line stably expressing the THAIC construct responds to TH in a TR dependent manner. Mean±SEM (n=3) * p<0.05 **p<0.01 by t-test.

DETAILED DESCRIPTION OF THE INVENTION

Figure 1:
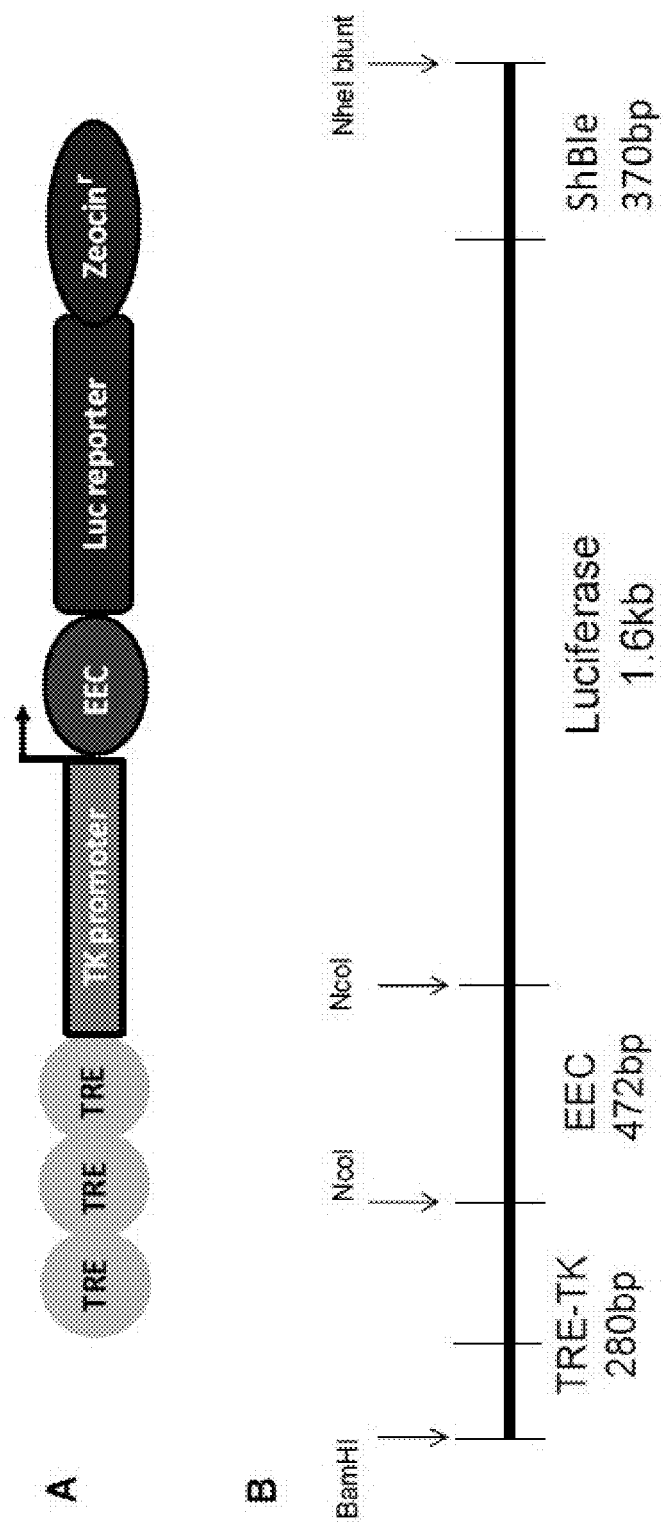
FIG. 1. The recombinant DNA construct (A) Schematic depiction of the targeting construct. TK promoter: thymidine kinase minimal promoter; TRE: thyroid hormone response elements; EEC; expression enhancer cassette Luc reporter-zeocin sequences encoding a Luciferase/zeocin resistance fusion protein. (B) Structure of the targeting construct generated in the pt2-BH vector. The coding sequence encodes Luciferase (62 kDa) fused to ShBle (14 kDa) allowing selection based on zeocin resistance.

To create a transgenic animal as well as cells and tissues that allow assessing thyroid hormone action even in vivo, a construct comprising combination of recombinant DNA elements was generated as a highly sensitive tool to monitor thyroid hormone (TH) action in transgenic animals and cultured cells (FIG. 1).

The recombinant construct that allows assessing TH action even in vivo is characterized by the following: the construct comprises a thyroid hormone responsive segment that is responsive to thyroid hormone dependent action via thyroid hormone receptors; a minimal promoter with tissue independent, ubiquitous expression in mammalian tissues with minimal/lacking responsiveness to transcription factors beyond those that are required to form the basic transcriptional complex; a coding region encoding a reporter gene that amount of which can be sensitively detected in vivo in live animals, ex vivo in tissue samples and in vitro in cultured cells; an expression enhancer cassette to promote the activity of the minimal promoter driven transcriptional unit; insulators that isolate the thyroid hormone responsive transgenic cassette from the neighbouring chromosomal regions.

In an embodiment the TR, when no TH binds thereto, forms a complex with corepressor molecules and acts as a TRE dependent repressor of gene transcription after binding to the TRE. When TH is present, the liganded TR forms complex with coactivator proteins. The TR-TH-coactivator complex bound to the TRE mediates the transcriptional effects of thyroid hormone via the thyroid hormone responsive segment. Preferably the binding of the TR-TH-coactivator complex to the TRE upregulates the promoter and thereby the expression of a gene driven by said promoter. In the present invention the promoter is preferably a minimal promoter and/or is preferably a ubiquitous promoter. In a preferred embodiment the promoter is operably linked to an enhancer sequence as described above or herein.

The TH is added during a measurement or assessment of the TH action in vivo or ex vivo or in vitro. Therefore by keeping the TH level at a constant or between ranges the effect of the TR expressed in the cells in which the construct is present and functions can be obtained. In this embodiment TH action can be indicated that represents a net result of TH transport, TH metabolism and TR mediated events.

When altering the level of TH in vivo or ex vivo or in vitro results in no alteration of the expression of the basic expression level measured in a control system it indicates that the cell expressing the reporter does not express TR. In this embodiment the presence or absence of TR expression of a cell may be determined. When TR is not expressed in the cells and/or when no TH is present no TR-TH-coactivator complex is formed and thereby a basic level expression of the reporter can be detected.

TR expression can be endogenous TR expression.

In a further similar embodiment the assessment method is also useful to monitor TR expression in a cultured cell line e.g. mammalian cell line producing TR e.g. high levels of TR for preparative or therapeutic purpose. In this embodiment TR expression is provided in said cells by an expression construct. In principle any appropriate means for TR expression is useful in the present invention.

If the level of TR expression is known the results of the measurement report directly on the TH action. In any case the level of the TR-TH complex defines the level of expression of the reporter.

In these settings it is important that TR expression is independent from the expression of the reporter.

In vivo imaging of TH action in live animals can be performed using an In Vivo Imaging System that allows repeated measurements, time course studies or determination of the effects of different TH analogues or different doses of the same derivative in different tissues, including the BAT, intestine, skin and salivary gland.

This can be also applied ex vivo on organs or tissue slices.

Below elements and function of the construct are discussed.

Thyroid hormone response element (TRE)

To ensure high responsiveness to thyroid hormone, one or more thyroid hormone response element (TRE) which is/are sufficiently sensitive to provide an appropriate level of thyroid hormone dependent regulation of the reporter expression upon binding of a complex comprising TR and TH is applied. In a particular embodiment the TRE is applied in triplicate.

The consensus TRE half site is AGGTCA spaced by 4 nucleotides followed by the second AGGTCA half site (TRE DR-4) (7). Less typical TREs are represented by inverted palindromic or palindromic half sites (e.g. F2 or Pal). The DR-4 is equally potent both for TRα and TRβ and binds the most typical form of liganded TR, the TR-RXR (Retinoid-X-Receptor-Receptor) heterodimer. In contrast, the F2 type TRE serves predominantly TRβ homodimers and Pal binds TR/RXR very poorly (7). Thus DR-4 provides a preferred option to put a reporter gene under potent and TR-dependent but not TR isoform selective response to thyroid hormone. In principle any TRE can be used in the present invention, however, there are TREs which are particularly used herein.

Within the construct one or more TREs and optionally flanking, separator or linker sequences form a part of the construct called herein a thyroid response segment. The function of this segment is to render the expression of the reporter sensitive to binding of a complex comprising TR and TH and, if necessary or desired, other coregulator proteins which may be part of or may bind to said complex. Such a TRE provides a positive regulation by TH. A negatively regulated TRE is optionally or preferably not contemplated as an embodiment of the present invention. In lack of TH binding the TR and if necessary or desired, other coregulator proteins act as a repressor (or act as repressors) on the TRE. Optionally, if a TR and/or a TRE functions in any other way it is not considered as an embodiment of the present invention.

Promoters

A promoter in the construct of the invention is functionally i.e. operably linked to the thyroid hormone response segment and more particularly to the one or more TRE. The promoter drives the transcription and/or expression of the reporter and thereby provides a functional link between the TRE and the reporter. Thereby the activity of the promoter is regulated by the activated form of thyroid hormone, T3, only in cells endogenously or transiently/stably overexpressing TR. The lack of TH action in a cell or if no TH action is measured in the cell, it is or may be indicative of the lack of TR in said cell.

The promoter has to be sufficiently strong to provide a signal via the reporter. To that purpose the promoter is (preferably) linked to an enhancer which is typically located downstream from the promoter.

The promoter is preferably a promoter which is capable of driving expression in a wide variety of mammalian tissues, or all mammalian tissues, ie. a ubiquitous promoter. For example the promoter is a promoter that is functional in all mammalian tissues where it is expressed. Selection of an appropriate promoter is, based on his/her knowledge and the teaching provided herein, within the skills of a person skilled in the art. A useful guidance may be provided in "A promoter-level mammalian expression atlas" The FANTOM Consortium and the RIKEN PMI and CLST (DGT) (16).

A preferred promoter is a Thymidine kinase (TK) minimal promoter, e.g. that of the Herpes simplex virus, that is capable to run ubiquitous transcription in any mammalian cell type.

Enhancers

Enhancers are able to activate expression of target genes in cis. In the present construct an enhancer is part of the construct and functionally strictly linked to the promoter. The expression enhancers typically contain intronic sequences that enhance transcription and promote most of the steps of mRNA metabolism (17). Enhancers suitable for the construction of a recombinant cassette according to the invention are able to optimize heterologous mRNA and thus protect it against elimination by the host cell. As an example, 3' to the 3×TRE-TK promoter unit there is an expression enhancer cassette that contains the untranslated leader (exon 1)-HTLV-1 R-Synthetic Rabbit β-globin-based 3' intron-intron unit e.g. of the NTC8681 vector (purchased from Nature Technology Corporations). To test the power of another enhancer to promote in vivo expression of the TRE-TK driven luciferase, new transgenic lines should be created using new targeting cassettes containing the enhancer to be tested. Preliminary data could be also obtained in cell culture via transient transfection of the new targeting construct, but only the generation of novel lines of transgenic animals will show how the enhancer embedded into a specific region of the chromosome will function.

Reporters

Beyond the used Luciferase reporter, fluorescent proteins could be also applied both ex vivo and in vivo. In live animals, both luciferase and fluorescent reporters can be detected. However, the detection of bioluminescence is considered to be more sensitive than that of fluorescence. For the detection of fluorescence, the animals need to be exposed to light of specific wavelength and the reporter needs to be located in superficial tissues. Specific injected fluorochromes are detectable with tomography in more embedded tissues if their emission is in the far red wavelength as the absorption of this type of light is less efficient in tissues. Discovering or engineering novel fluorescent proteins that are excited and emitting in the far red wavelength would highly enhance the detectability of fluorescent reporter proteins in deeply localized tissues.

Protein reporters that can be detected by light-microscopic approaches based on the formation of coloured products (e.g. beta-Gal) cannot be used for in vivo detection in live animals.

Resistance Markers

In another embodiment the recombinant DNA construct of the invention further comprises a sequence coding for a resistance marker, preferably a positive resistance marker to ensure the successful transformation of the cells or animals with the construct.

In a preferred embodiment the expression of the sequences coding for the reporter and of the resistance marker are operably linked, e.g. said sequences are fused to each other in frame. Preferably the recombinant DNA construct also comprises a polyadenylation segment downstream from the coding sequences. The advantage of this embodiment is that the expression of the reporter is linked to the expression of the resistance marker which further ensures the selection and/or maintenance of the cells containing the recombinant construct in the presence of a compound to which the resistance marker provides resistance.

In certain embodiments the resistance marker is an antibiotic resistance marker, e.g. a broad spectrum antibiotic that is effective against most bacteria, filamentous fungi, yeast, plant, and animal cells, or a narrow spectrum antibiotic effective against the cell type in which the reporter is expressed.

In an embodiment the antibiotic is a glycopeptide antibiotic. In a highly preferred embodiment the glycopeptide antibiotic belongs to the bleomycin family of antibiotics which is highly preferably a zeocin resistance, in particular a ShBle zeocin resistance antibiotic.

In a preferred embodiment the antibiotic is encoded in an antibiotic resistance cassette, which is highly preferably a zeocin resistance cassette, in particular a ShBle zeocin resistance cassette.

Insulator Sequences

The construct described above is flanked by insulator sequences.

"Insulator" is the name given to a class of DNA sequence elements that possess a common ability to protect genes from inappropriate signals emanating from their surrounding environment. Insulators can act by blocking the action of a distal enhancer on a promoter, if the insulator separates the promoter from the distal enhancer. Alternatively insulators protect genes by acting as "barriers" that prevent the advance of nearby condensed chromatin that might otherwise silence expression. Some insulators are able to act both as enhancer blockers and barriers (18).

In the present invention both role of the insulators may be preferred, in particular the barrier function.

However, blocking of a distal enhancer which may influence the reporter expression in the present construct may also be advantageous. The cassette preferably allows ubiquitous expression in mammalian cells in a cell-type independent manner.

Imprinted genes are expressed either from maternal or fraternal alleles. To ensure this, imprinted gene clusters are flanked by insulator sequences that help to isolate them from the transcriptional activity of flanking regions. An example for this is the Igf2/H19 locus that is known to function as an insulator (19).

The recombinant DNA construct thus created is suitable to be used for the generation of transgenic animals with application of an appropriate means of introducing the construct into a cell. The complex structure of the construct and the interactions between the elements of the construct result in a successful integration into the genome and ensure that the construct remains functional when integrated.

Although transient expression of a TRE containing recombinant construct in a cell line may have been reported earlier, stable integration into the genome of a construct which actually provides TH responsive expression of a reporter and thereby assessment of TH action requires a more complex approach to arrive at a functional solution.

The complexity of integration and regulation of the expression of a transgene in an adult transgenic animal may be illustrated by some of the several unsuccessful attempts of the present inventors to generate a thyroid hormone action indicator transgenic animal. Despite successful integration into the genome in different transgenic mouse lines, the cassettes either remained silent in all tissues, or resulted in tissue-restricted expression (e.g. in the muscle or in the thalamic brain region) with no response to thyroid hormone. Earlier constructs are shown in Table 1.

TABLE 1

Examples of non-working recombinant constructs

| TRE | promoter | reporter | insulator |
|---|---|---|---|
| 3xTRE | TK | dEYFP(destabilized EYFP) | |
| 3xTRE | Rosa26 | dEYFP | |
| 3xTRE | TK | Luc (originated from pGL3-basic of Promega) | H19 |
| 3xTRE | TK | Luc (originated from pGL3-basic of Promega) | chicken lysosime insulators |

The invention will be further described by way of exemplary embodiments.

To create a transgenic animal that allows assessing thyroid hormone action in vivo, a unique combination of recombinant DNA elements was first generated as a highly sensitive tool to monitor TH action in transgenic animals and cultured cells (FIG. 1).

To ensure high responsiveness to thyroid hormone, the DR4 thyroid hormone response element (TRE) of the 5' flanking region of human dio1 gene (20) that is considered to be the most sensitive response element to thyroid hormone-mediated induction was placed in triplicate 5' to the Thymidine kinase (TK) minimal promoter of the Herpes simplex virus that is capable to run ubiquitous transcription in any mammalian cell type. 3' to the 3×TRE-TK promoter unit a complex expression enhancer cassette that contains the untranslated leader (exon 1)-HTLV-1 R-Synthetic Rabbit β-globin-based 3' intron-intron unit of the NTC8681 vector (purchased from Nature Technology Corporations) was inserted. 3' to this cassette a codon optimized and methylation resistant dCpG Luciferase coding region was inserted to allow optimal performance in mammalian cells that was fused to ShBle (originated from the pMOD Luc-ShS v02 plasmid, purchased from Invivogen) that provides resistance against Zeocine followed by an EF1 pAn polyadenylation cassette. The cassette was assembled in a pWHERE vector (purchased from Invivogen) and it was flanked by the H19 insulators of the vector. The targeting cassette was subcloned between the ITR transposase recognition sequences of the pt2-BH expression vector as a HindIII(blunt)-NotI fragment (FIG. 1).

The cassette allows ubiquitous expression in mammalian cells in cell-type independent manner. The activity of the promoter is regulated by the activated form of thyroid hormone, T3, only in cells endogenously expressing TR.

To generate transgenic mice with the recombinant DNA construct, a transposon based delivery was applied using the Sleeping Beauty system (21). The Sleeping Beauty system is particularly useful for the generation of stable transgenic animal lines as it is present only transiently by the integration of the recombinant cassette. This guarantees that the position of the cassette will not change afterwards and the transgenic animal lines remain stable during breeding. Other plasmid systems and viral vectors may also be used to introduce the recombinant DNA construct of the invention, especially when a stable integration is not necessary.

For generating transgenic founders, the pronucleus of fertilized oocytes were injected with picoliter volumes of a mixture containing the plasmid harbouring the targeting cassette (1 ng/μl) and the in vitro transcribed mRNA encoding the Sleeping beauty transposon (5 ng/ul).

Founders were identified using TaqMan assay with a Luciferase probe and crossed with wild/type FVB/N mice followed with inbred coupling of F1 generation. The F2 generation was used for Luciferase assays. TaqMan assay assisted determination of transgene dosage in all lines suggested that the transgenic cassette was incorporated in a single copy. The mouse model shows stable performance already in the 6th generation.

Characterization of the #4, 18 and 23 lines identified thyroid hormone (5 ug of T4/day/mouse for 3 days) induced induction of Luciferase expression in various tissues of homozygote males. Line #4 showed induction both in various brain regions and in different peripheral tissues (skeletal muscle, bone, intestine, liver and heart) that included a striking response in the BAT. Line #23 showed an intense response to TH in the pituitary and hypothalamus, while #18 showed a high basal expression and an intense response in the pituitary.

Thus #4 is a line suitable for general use and shows special expression strength in the BAT. Line#23 is highly suitable to study TH response in the hypothalamus and pituitary. Line #18 could be used in the brain when a higher basal activity is required.

To further assess the utility of the recombinant DNA construct it was also introduced into the human HEK293 cell line to generate a stably transfected in vitro system for TH action.

The generated transgenic mouse model can be used to semi-quantitatively assess tissue and cell-specific in vivo thyroid hormone action in tissues of sacrificed animals or in live animals based on thyroid hormone dependent expression of a Luciferase reporter the transcription of which is fully dependent on endogenously expressed intact wild-type TRs and coregulators machinery of TH action. Thyroid hormone action can be measured in tissues of sacrificed animals by detecting the translated Luciferase-ShBle fusion protein by luciferase assay or cytochemistry. Expression of the reporter mRNA can be assessed by quantitative PCR or in situ hybridization. Ex vivo TH action can be assessed in a tissue sample or tissue explant of a transgenic animal either by using an In Vivo Imaging System or by detecting the translated Luciferase-ShBle fusion protein by luciferase assay or cytochemistry. Similarly to in vivo TH action, ex vivo TH action can also be assessed by measuring the reporter mRNA by quantitative PCR (qPCR) or in situ hybridization. In vitro TH action can be measured in cultured cells containing THAIC by the same methods.

The generated transgenic animal model provides the first animal model allowing the live assessment of in vivo TH action.

In vivo imaging of TH action in live animals can be performed using an In Vivo Imaging System that allows repeated measurements, time course studies or determination of the effects of different TH analogues or different doses of the same derivative in different tissues, including the BAT, intestine, skin and salivary gland. This can be also applied ex vivo on organs or tissue explant or in vitro on cell culture.

In some embodiments in vivo TH action is assessed by detecting the level of the expression of the reporter in a transgenic animal live using an In Vivo Imaging System based on thyroid hormone dependent expression of a Luciferase reporter or in tissue samples of said animal by detecting the translated Luciferase-ShBle fusion protein by luciferase assay or cytochemistry or by detecting Luc mRNA by real time qPCR.

In some embodiments ex vivo TH action is assessed by detecting the level of the expression of the reporter in tissue samples of the transgenic animal using an In Vivo Imaging System based on thyroid hormone dependent expression of a Luciferase reporter or by detecting the translated Luciferase-ShBle fusion protein by luciferase assay or cytochemistry or by detecting Luc mRNA by real time qPCR.

In some embodiments ex vivo TH action is assessed by detecting the level of the expression of the reporter in cells comprising the recombinant construct of the invention using an In Vivo Imaging System based on thyroid hormone dependent expression of a Luciferase reporter or by detecting the translated Luciferase-ShBle fusion protein by luciferase assay or cytochemistry or by detecting Luc mRNA by real time qPCR.

The transgenic animal model also provides an ideal source of cells to generate T3-responsive Luciferase expressing primary cultures and cell lines from various tissues. Zeocin can be used to ensure that the TH-responsive Luciferase cassette is maintained during culturing and replating.

The transgenic animal model can be useful for the pharmaceutical industry for the in vivo assessment of TR agonists or antagonists, modulators of coregulators or thyroid hormone transporters produced to take advantage of the beneficial effect of TH action (e.g. weight loss, lowered cholesterol level) without evoking hazardous side effect of TH (e.g. lipogenesis and tachycardia). The model also allows fast and efficient testing of subtype or tissue selective agonists or antagonists of TRs.

The transgenic animal model provides a powerful tool to understand TH action in the BAT. Since this tissue is a major site locus of energy dissipation, it represents an intensively studied target of obesity research.

Thus the transgenic animal model is a valuable tool for obesity research.

The transgenic animal lines can be crossed with various transgenic mouse models that harbour deletion, mutations or Cre-recombinase targetable floxed versions of thyroid hormone receptors, TH metabolizing deiodinase enzymes, TH transporters or any other genes that might interfere with TH economy. The transgenic lines resulting from these crossings will allow the assessment of the impact of the modified gene function on TH action. Crossing with TR specific mutants can further facilitate the use of the transgenic mice for testing the receptor subtype specific agonists and antagonists.

The transgenic animal model will also be of great benefit for discovery-driven scientific studies aimed to better understand cell-type specific thyroid hormone action to decipher underlying mechanism of the regulation of cell proliferation, energy homeostasis and any other symptom/condition associated with altered thyroid hormone economy (e.g. nonthyroidal illness syndrome, testing of thyroid hormone combination therapy).

The THAIC DNA construct can be used to generate transgenic animals and cell lines including cells with stable expression of the targeting cassette in order to assess TH action. Cells may also be isolated from the transgenic animal and modulators of TH action can be studied also in vitro under culture conditions.

A transgenic mouse comprising the THAIC DNA construct (THAIM) may be used as an animal model to understand the mechanisms underlining various diseases related to deficient TH action. Alteration of TH action is a hallmark of various human symptoms, e.g. resistance to thyroid hormone (RTH) is characterized by mutated TRα or TRβ (22,23), while impaired TH transport is associated with X-linked psychomotor retardation (Allan-Herndon-Dudley Syndrome, AHD) (24,25). TH action is also changed in nonthyroidal illness syndrome (NTIS) (5,26), after TH replacement therapy (27) and TH action also affects the generation of obesity (28).

Crossing THAIM with a mouse, wherein the mouse is a mouse model of RTH or wherein the mouse comprises a modification which mimics human RTH or wherein the mouse has a mutation in TRα or TRβ (i.e. mouse models already established for RTH; both for TRα or TRβ mutant versions) or introducing THAIC in such a mouse are possible ways to create a highly useful animal model to study the mechanisms of human RTH, wherein TH action and agents affecting TH action, isoforms of TR subtypes and coregulators of the TRs as well as potential therapeutic agents may be studied. Mouse models of human TR mutations are reviewed by Ortiga-Carvalho (23). Mutations in TRβ are e.g. Thr337del, Thr448fsX17, Glu124Gly and Gly125Ser and Arg429Gln. Mutations in TRα that result in a mouse model phenotypically similar to patients with TRα mutations are e.g. Pro398His, Thr394fsX17, Leu400Arg, Arg384Cys.

Similarly, crossing THAIM with a mouse serving as an animal model of ADH or introducing THAIC in such a mouse are possible ways to create a highly useful animal model to study the Allan-Herndon-Dudley Syndrome wherein TH action and agents affecting TH action as well as isoforms of TR subtypes and coregulators of the TRs and potential therapeutic agents may be studied. Currently available mouse models of ADH are mice having MCT8 (monocarboxylate transporter 8) deficiency, such as MCT8 knockout mice.

Evoking NTIS (e.g. by LPS, see (29)), obesity or aging in THAIM or in a mouse serving as animal model of a TH action related disease or condition and comprising THAIC could provide significant advancement in the treatment or understanding of these syndromes and conditions and can be used as an animal model of these syndromes and conditions.

The invention will be further described by way of the following examples.

EXAMPLES

Example 1

Effect of exogenous T3 on luciferase activity in vivo

Figure 2:
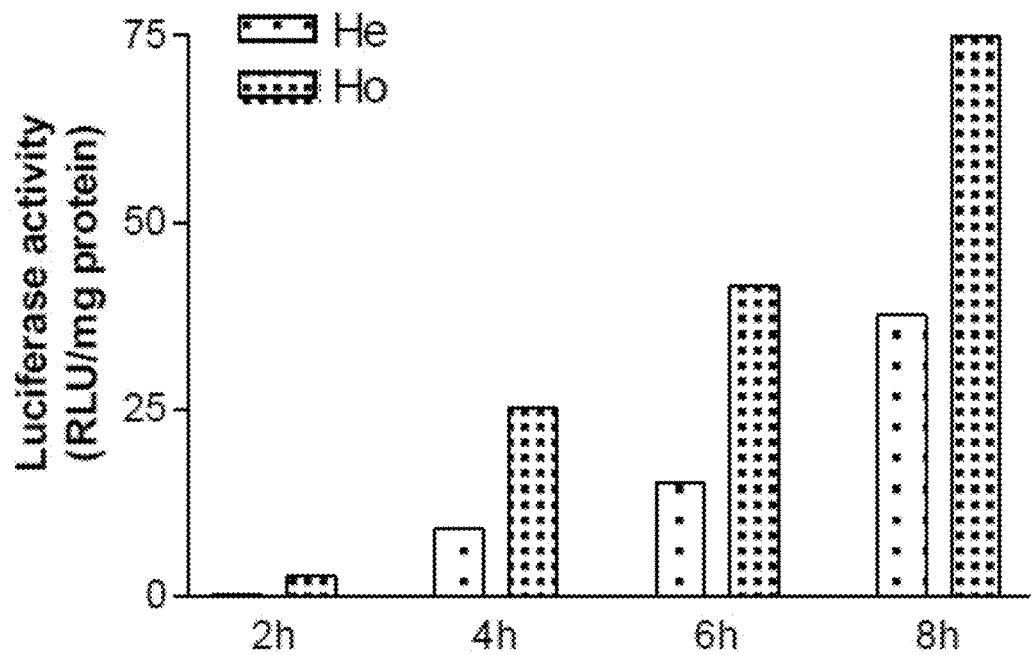
FIG. 2. Luciferase activity of the transgenic animal model directly depends on copy number T3 was administered to mice from the #4 line (1 μg/g bw, i.p.) and luciferase activity was assessed by luciferase assay at four different time points in the brown adipose tissue. Homozygotes showed a 2 fold higher Luciferase activity than heterozygotes (means of two animals of each group).

Administration of 1 µg/g bw T3 i.p. to males of line #4 resulted in a continuous increase of luciferase activity assessed by luciferase assay at four different time points up to 8 hours in the brown adipose tissue. The activity showed a clear dependence on copy number of transgene since homozygotes showed ~2 fold higher activity compared to heterozygotes (FIG. 2).

Example 2

Cold Induced T3 Generation in the Interscapular BAT (iBAT)

Cold induction is a well-established condition to induce T3 generation in the iBAT (30). A previously established and published protocol was used to evoke cold stress in mice (31) to study whether a physiological increase of local T3 availability can result in an increase of luciferase expression in line#4 that demonstrated thyroid hormone responsiveness in the iBAT (Table 2).

TABLE 2

Effect of thyroid hormone on Luciferase activity in different tissues of the transgenic mice.

| Tissue | basal (RLU/mg protein) | induced (RLU/mg protein) | Fold (mean ± SEM) | p value |
|---|---|---|---|---|
| Table 2A Effect of T4 on Luciferase activity in different tissues of THAIM line #4 | | | | |
| Pituitary (Pit) | 0.337 | 0.791 | 2.3 ± 0.16 | *0.0001 |
| Mediobasal Hypothalamus (MBH) | 0.206 | 0.368 | 1.8 ± 0.20 | *0.013 |
| Hippocampus (HC) | 0.060 | 0.116 | 1.9 ± 0.03 | *0.0001 |
| Hypothalamus (HT) | 0.377 | 0.488 | 1.3 ± 0.08 | *0.031 |
| Cortex (CTX) | 0.194 | 0.359 | 1.9 ± 0.30 | *0.035 |
| Cerebellum (CER) | 0.938 | 2.162 | 2.3 ± 0.41 | *0.019 |
| Liver | 0.002 | 0.005 | 1.9 ± 0.14 | *0.0007 |
| Heart | 0.004 | 0.030 | 8.5 ± 0.31 | *0.0001 |
| iBAT | 0.028 | 1.820 | 64.6 ± 8.1 | *0.0002 |
| Bone | 0.031 | 0.066 | 2.2 ± 0.18 | *0.0015 |
| Muscle | 0.025 | 0.276 | 11.2 ± 5.7 | *0.0041 |
| Mandibular salivatory gland (MSG) | 0.052 | 0.399 | 7.6 ± 2.60 | *0.044 |
| Thyroid | 0.115 | 0.176 | 1.5 ± 0.07 | *0.002 |
| Testicle | 4876 | 4086 | 0.8 ± 0.06 | 0.108 |
| Intestine | 4.571 | 9.480 | 2.1 ± 0.30 | *0.012 |
| Skin | 0.696 | 2.798 | 4.0 ± 0.76 | *0.001 |
| Table 2B Effect of T4 on Luciferase activity in different tissues of THAIM line #23 | | | | |
| Pit | 1.932 | 16.926 | 8.8 ± 0.62 | *0.0001 |
| MBH | 0.142 | 0.240 | 1.7 ± 0.29 | 0.103 |
| HC | 0.035 | 0.040 | 1.1 ± 0.32 | 0.756 |
| HT | 0.053 | 0.144 | 2.7 ± 1.35 | 0.338 |
| CTX | 0.037 | 0.065 | 1.8 ± 0.21 | 0.103 |
| CER | 0.012 | 0.023 | 1.9 ± 0.28 | *0.045 |
| Liver | 0.004 | 0.004 | 1.7 ± 0.19 | 0.793 |
| Heart | 0.008 | 0.003 | 1.0 ± 0.47 | — |
| iBAT | 0.005 | 0.038 | 7.2 ± 1.54 | *0.007 |
| Bone | 0.010 | 0.011 | 0.9 ± 0.56 | 0.934 |
| Muscle | 0.004 | 0.003 | 0.7 ± 0.18 | |
| Table 2C Effect of T4 on Luciferase activity in different tissues of THAIM line #18 | | | | |
| Pit | 0.066 | 0.540 | 8.2 ± 0.36 | *0.0001 |
| MBH | 0.372 | 0.602 | 2.2 ± 0.25 | *0.005 |
| HC | 2.308 | 3.756 | 2.1 ± 0.25 | *0.013 |
| HT | 0.755 | 1.589 | 2.8 ± 0.35 | *0.004 |
| Cortex | 1.617 | 2.586 | 1.9 ± 1.18 | *0.005 |
| Cerebellum | 0.045 | 0.063 | 1.8 ± 0.31 | 0.073 |
| Liver | | | no expression | |
| Heart | | | | |
| iBAT | | | | |
| Bone | | | | |
| Muscle | | | | |
| MSG | | | | |
| Thyroid | | | | |
| Testicle | | | | |
| Intestine | | | | |
| Table 2D Effect of T3 on Luciferase activity in THAIM line #4 | | | | |
| Liver | 0.003 | 0.017 | 5.0 ± 0.6 | *0.009 |
| Heart | 0.006 | 0.284 | 45.9 ± 5.65 | *0.002 |
| Effect of T3 on Luciferase activity in THAIM line #23 | | | | |
| MBH | 0.180 | 2.222 | 12.31 ± 2.4 | *0.003 |

Basal and thyroid hormone induced values and fold changes (induced/basal) of Luciferase activities in tissues of sacrificed animals (Mean±SEM, n=4). P values of t test (basal vs. induced) are provided, * represents statistical significance. (A, B, C) T4 treatment (5 ug/mouse/day for 3 days; i.p.) in mouse lines #4, 18, and 23. Basal activity levels in #18 are higher than other two lines. MSG: mandibular salivatory gland (D) T3 treatment (1 µg/g bw i.p.) in line #4, effect on peripheral organs. The effect of T3 on Luciferase expression is more robust, than that of T4 (Mean±SEM, n=4). All experiments were performed on homozygote males.

Figure 3:
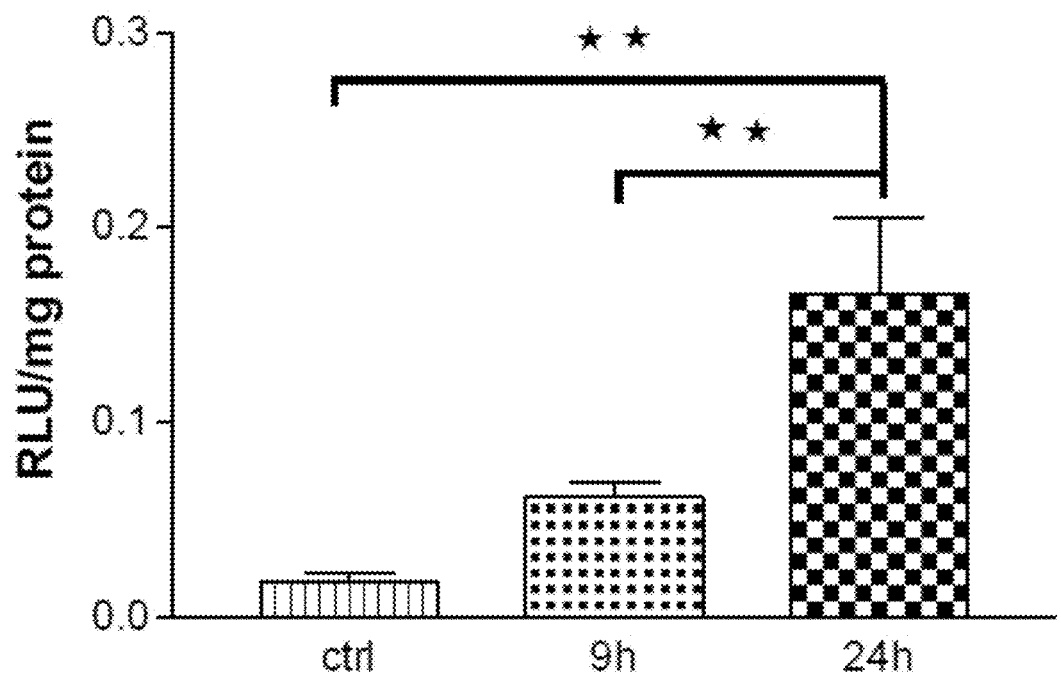
FIG. 3. Luciferase activity is up-regulated in the brown adipose tissue of cold stressed transgenic mice Luciferase activity shows a tendency to elevate in BAT after 9 hours at 4° C. and is significantly increased after 24 hour cold stress. **P<0.01; by one way ANOVA followed by Newman-Keuls post-test. Data are shown as Mean±SEM (n=5).

Cold induction continuously increased luciferase activity in the studied period up to 24 hours demonstrating that the incorporated transgenic cassette is responsive to physiological changes of local T3 concentration (FIG. 3). The power of THAIM was demonstrated to study regulation of iBAT by using unilateral sympathetic denervation to study TH action in the absence of sympathetic inputs, since these two signalling pathways are major synergistic regulators of iBAT function. The local activation of type 2 deiodinase (D2)-mediated thyroid hormone signalling in iBAT of THAIM#4 evoked a 2.5-fold increase in luciferase reporter mRNA expression in the intact lobe as assessed by quantitative PCR (for details see also Example 3) after 9 h cold-exposure. This response was abrogated by unilateral sympathetic denervation of the iBAT, which also prevented cold-induction of D2 activity. Notably, luciferase reporter mRNA expression was maintained in the denervated iBAT lobe compared to the intact lobe at room temperature. These data highlight that THAIM is suitable to study adrenergic stimulation induced TH action in the iBAT and provides mechanistic details on the mechanisms allowing the adaptation of TH action to conditions when sympathetic signalling is impaired.

Figure 4:
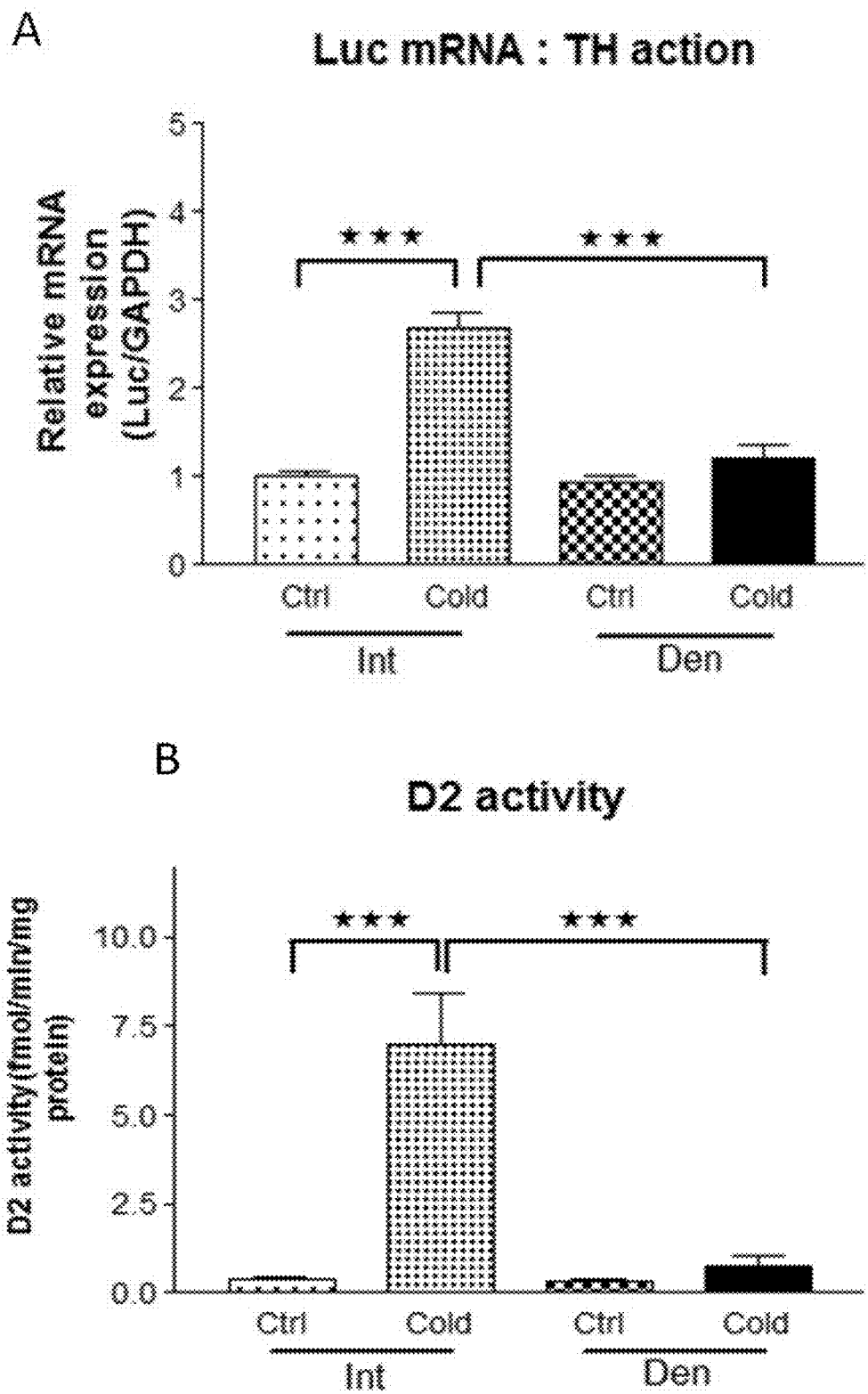
FIG. 4. Luciferase expression in the cold induced interscapular brown adipose tissue of transgenic mice depends on sympathetic innervation (A) Luciferase mRNA expression significantly increased by 9 h cold challenge at 4° C. on the intact side of iBAT. TH action was not influenced by 9 h cold on the denervated side. Despite sympathetic denervation, luciferase expression did not decrease at room temperature in the denervated lobe compared to the intact lobe. (B) Denervation abolished the cold induced increase of the T3 generating type 2 deiodinase activity in iBAT, while it did not influenced the D2 activity at room temperature. *** p<0.001; repeated measure ANOVA followed by Newman-Keuls post-hoc test. Data are shown as Mean±SEM (N=6).

(FIG. 4). Unilateral denervation of sympathetic nerves innervating the iBAT has been performed as described in (32). Measurement of the activity of type 2 deiodinase was performed according to the American Thyroid Association Guide to investigating thyroid hormone economy and action in rodent and cell models (33)). THAIM #4 mice underwent unilateral denervation of sympathetic nerves innervating the BAT. Luciferase activity assay was performed using our established protocol (34) modified for tissue samples. Luciferase expression increased significantly by cold challenge at 4° C. on the intact side between controls vs. 9 h. This increase was abolished by denervation but TH action was maintained at room temperature (intact vs. denervated). (A). In the denervated samples, this was paralleled by abolished response of D2 activity to cold and maintenance of the basal D2 activity in the denervated lobe at room temperature (B).

This finding indicates that the model is suitable to study adrenergic stimulation induced TH action in the BAT.

Example 3

Detection of Luciferase mRNA as a Readout of TH Action in the Pituitary

We also studied whether detection of luciferase mRNA can be used to detect as a readout of TH action in the generated transgenic model. Injection of 1 µg/g bw T3 i.p. into the line #23 generated an ~50 fold induction of luciferase mRNA in the pituitary using TaqMan assay. TaqMan qPCR was performed on a ViiA 7 Real-Time PCR System (Life Technologies) according to the instructions of the manufacturer. In short, reverse transcription was performed with High Capacity cDNA Reverse Transcriptase Kit (Applied Biosystems by Life Technologies) and concentration of the cDNA was determined using the Qubit 2.0 Fluorometer with the Qubit ssDNA Assay Kit (Life Technologies). A custom Luciferase coding probe was used along with a commercially available probe for Glyceraldehyde-3-phosphate dehydrogenase (GAPDH), later used as housekeeping gene.

Figure 5:
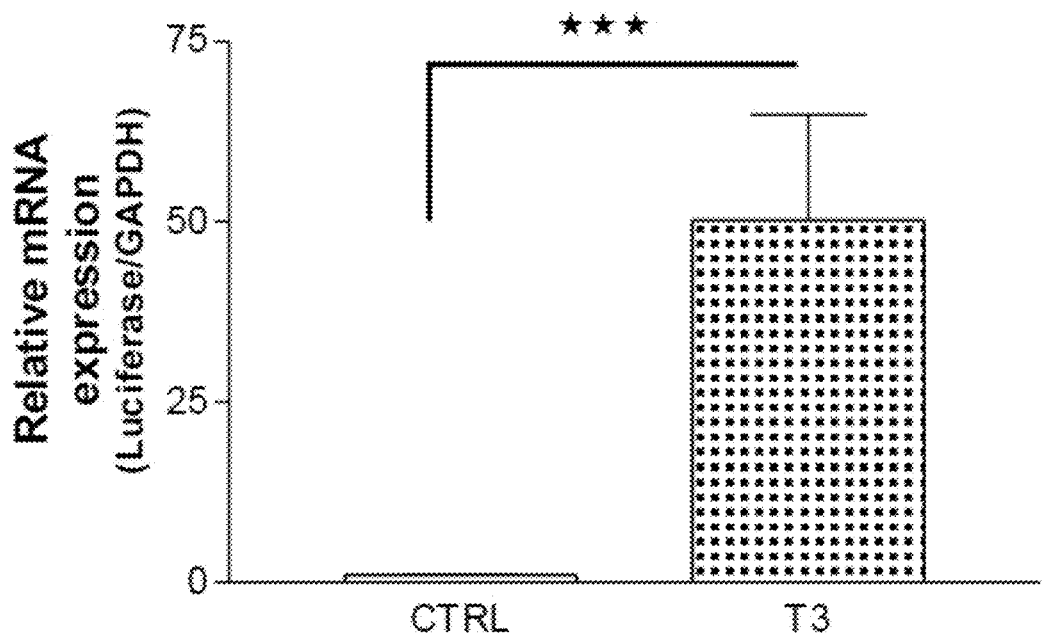
FIG. 5. Luciferase mRNA expression is up-regulated in the pituitary of T3 treated transgenic mice Luciferase mRNA level is robustly increased by T3-treatment in the pituitary of #23 THAIM mouse line. Expression was assessed with TaqMan assay, Luciferase expression level was denominated with GAPDH expression used as housekeeping gene. Mean±SEM (n=5) *** p<0.0001 by t test.

This demonstrated that qPCR can be also used to assay TH action in our model, providing the advantage of direct detection of transcriptional changes evoked by T3 action without waiting until the reporter gene is getting translated. (FIG. 5)

Example 4

Detection of TH Action in Brain Nuclei

Figure 6:
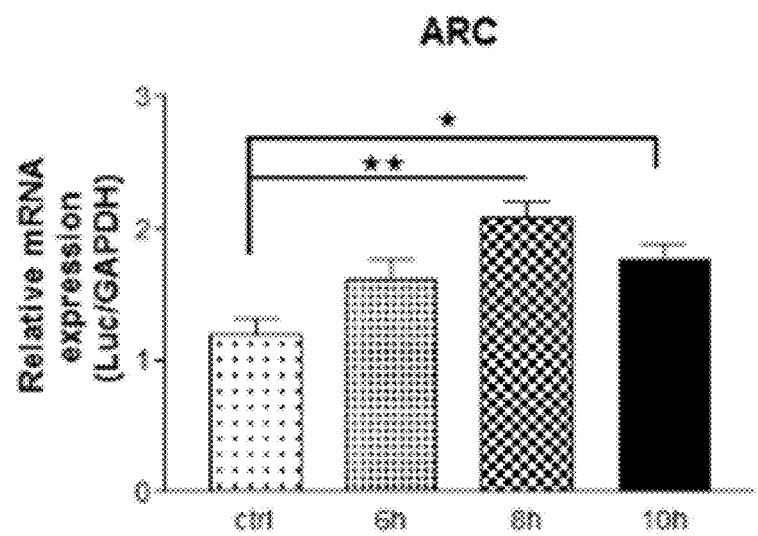
FIG. 6. Detection of TH action in microdissected brain samples in LPS challenge
Figure 6:
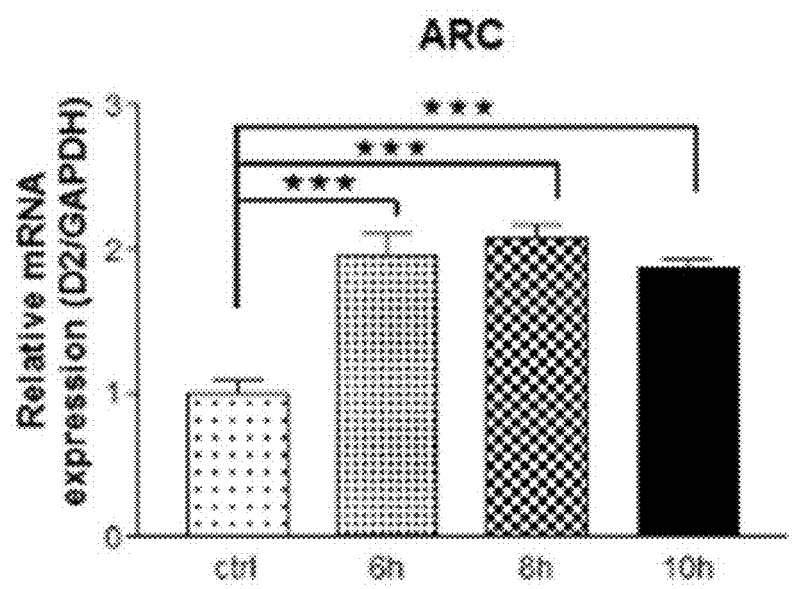
Figure 6:
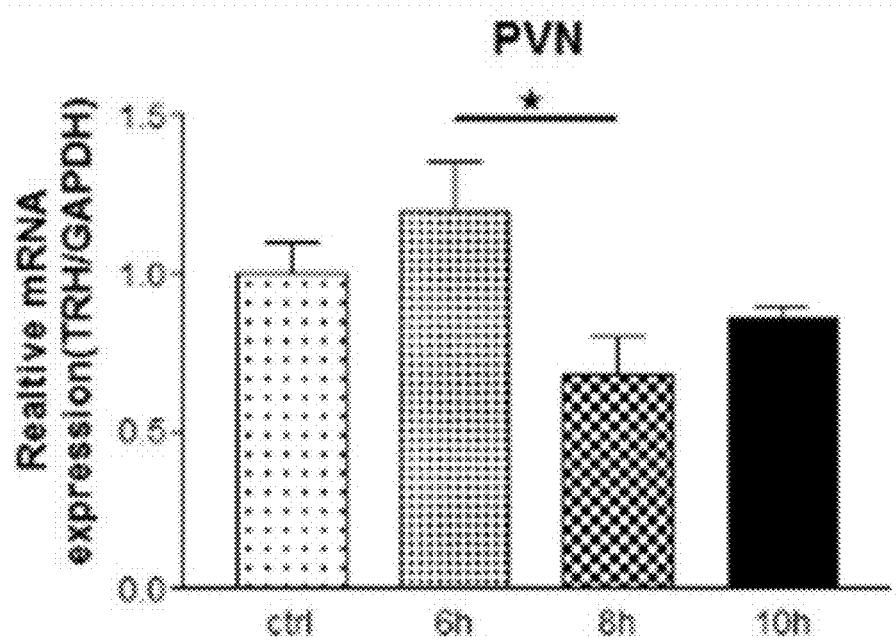

To determine changes of TH action in small tissue samples, e.g. in specific brain nuclei that are too small for direct measurement of their T3 concentration we applied a nonthyroidal illness syndrome model to THAIM #23 since under these conditions marked changes of TH action is expected in the hypothalmus, However, this phenomenon could not be directly studied before THAIM was generated. 150 µg bacterial lipopolysaccharide (LPS) or saline as control was injected i.p. and the animals were sacrificed 6, 8 and 10 h later. The hypothalamic arcuate nucleus-median eminence (ARC-ME) region and the paraventricular nucleus (PVN) were subjected to microdissection by punching hypothalamic slices. TH action was determined in the ARC-ME region of the hypothalamus where the axon terminals of the hypophysiotropic axons may sense local TH availability (FIG. 6). An increased luciferase mRNA level could be measured with quantitative PCR that reached statistical significance 8 h after the treatment (A). This was preceded by the elevation of D2 mRNA level in the same region (B). A marked decrease of TRH mRNA level was observed in the PVN of LPS treated animals 8 h after the treatment (C). These data demonstrate that THAIM is able to detect changes of TH action evoked by altered levels of endogenous TH even in very small brain regions. This could not be assessed before with other approaches. The obtained data revealed hypothalamic increase of TH action in an animal model of the human nonthyriodal illness syndrome that helps to explain the impaired response of the hypothalamo-pituitary-thyroid axis of his patient to falling TH levels.

Example 5

Testing TR Isoform Specific Agonists

We decreased the endogenous thyroid hormone levels in line #4 by administering methimazole and perchlorate (0.1% methimazole, 0.5% perchlorate) in the drinking water followed by the i.p. injection of 1.53 nM/g BW of GC-24, a TRβ specific agonist (35). Luciferase activity assay was performed using our established protocol (34) modified for tissue samples, that included treatment of mouse tissue with liquid nitrogen, followed by sonication. In vivo Luciferase imaging has been performed on an IVIS Lumina II In vivo Imaging System (PerkinElmer Waltham, Mass., USA) according to the instructions of the manufacturer. In the liver, a tissue where TRβ is the dominant isoform, Luciferase activity was increased-3-fold 24 h after the treatment while in the heart, where TRα expression is the predominant TH isoform, no significant change of luciferase activity could be detected, while T3 administration induced significant increase of luciferase activity in both tissues (FIG. 7). This finding demonstrates that the model provides a highly sensitive in vivo environment that allows the testing of the performance of TR isoform or tissue specific compounds that can facilitate industrial efforts to generate and market effective compounds to exert the beneficial effects of thyroid hormone treatment.

Example 6

In Vivo Detection of Luciferase

We also studied whether changes of TH action can be demonstrated in live animals using in vivo detection of Luciferase which approach allows repeated or time course measurements. Line #4 was injected i.p. 1 µg/g BW T3 i.p. and 24 h later with the Luciferase substrate luciferin. After 15 min, mice were anesthetized with ketamine followed by detection with NIS Lumina II In vivo Imaging System (PerkinElmer Waltham, Mass., USA). T3 induced very intense increase in reporter activity in the BAT and intestine. Reporter activity was also up-regulated in the mandibular salivary gland (MSG) and in the skin of the tail and foot pads (FIG. 8) demonstrating that the model can be used to detect TH action in live animals (A). THAIM could also detect physiological stimulus evoked live TH action in the iBAT after 24 h cold stress while TH action in cold skin remained unchanged under these conditions (FIG. 9).

Example 7

Cell Lines Transfected with the THAIC Recombinant DNA Construct

The THAIC construct was transfected to the human HEK293 cells along with a pCMV(CAT)T7-SB100 Sleeping Beauty transposon expressing vector and a mouse TRα encoding plasmid. Transfection and cell culturing of HEK293 cells was performed according to our established protocol (36). (FIG. 10)

(A) 100 nM T3 evoked an approximately 4-fold induction of Luciferase expression as assessed by Luciferase promoter assay. (B) We also used zeocin-assisted selection and obtained cultures stably expressing Luciferase and generated the HEK293-THAIC cell line stably expressing the TH action indicator construct of the THAM model. The reporter of the cell line is responsive to TH in a TR dependent manner. This demonstrates that the THAIC construct is also suitable to generate cell lines to monitor TH action in cultured cells including cells of human origin.

REFERENCES

1. Larsen P R, Ingbar S. The Thyroid. In: Wilson, Foster, eds. Textbook of Endocrinology. 8 ed. Philadelphia: W.B. Saunders, Co.; 1992:357-487.
2. Gereben B, Zavacki A M, Ribich S, Kim B W, Huang S A, Simonides W S, Zeold A, Bianco A C. Cellular and molecular basis of deiodinase-regulated thyroid hormone signaling. Endocrine reviews 2008; 29:898-938
3. Visser W E, Friesema E C, Jansen J, Visser T J. Thyroid hormone transport in and out of cells. Trends Endocrinol Metab 2008; 19:50-56
4. Oetting A, Yen P M. New insights into thyroid hormone action. Best Pract Res Clin Endocrinol Metab 2007; 21:193-208
5. Fekete C, Lechan R M. Central regulation of hypothalamic-pituitary-thyroid axis under physiological and pathophysiological conditions. Endocrine reviews 2014; 35:159-194
6. Lin J Z, Sieglaff D H, Yuan C, Su J, Arumanayagam A S, Firouzbakht S, Cantu Pompa J J, Reynolds F D, Zhou X, Cvoro A, Webb P. Gene specific actions of thyroid hormone receptor subtypes. PloS one 2013; 8:e52407
7. Velasco L F, Togashi M, Walfish P G, Pessanha R P, Moura F N, Barra G B, Nguyen P, Rebong R, Yuan C, Simeoni L A, Ribeiro R C, Baxter J D, Webb P, Neves F A. Thyroid hormone response element organization dictates the composition of active receptor. The Journal of biological chemistry 2007; 282:12458-12466

8. Hedley A A, Ogden C L, Johnson C L, Carroll M D, Curtin L R, Flegal K M. Prevalence of overweight and obesity among U S children, adolescents, and adults, 1999-2002. JAMA 2004; 291:2847-2850
9. Wolf A M, Colditz G A. Current estimates of the economic cost of obesity in the United States. Obes Res 1998; 6:97-106
10. Tóth E, Nagy B. Az elhízás egészséggazdaságtani megközelítése. Egészségügyi Gazdasági Szemle (4) 2004:41-48
11. Bates H M. Prevalence of hyperlipidemia in a large sample population. Journal of cardiovascular pharmacology 1982; 4 Suppl 2:S196-200
12. Quignodon L, Legrand C, Allioli N, Guadano-Ferraz A, Bernal J, Samarut J, Flamant F. Thyroid hormone signaling is highly heterogeneous during pre- and postnatal brain development. Journal of molecular endocrinology 2004; 33:467-476
13. Nucera C, Muzzi P, Tiveron C, Farsetti A, La Regina F, Foglio B, Shih S C, Moretti F, Della Pietra L, Mancini F, Sacchi A, Trimarchi F, Vercelli A, Pontecorvi A. Maternal thyroid hormones are transcriptionally active during embryo-foetal development: results from a novel transgenic mouse model. Journal of cellular and molecular medicine 2010; 14:2417-2435
14. Zhang C, Kim S, Haney J W, Larsen P R. Further characterization of thyroid hormone response elements in the human type 1 iodothyronine deiodinase gene. Endocrinology 1998; 139:1156-1163
15. Lazar M A. Thyroid hormone action: a binding contract. The Journal of clinical investigation 2003; 112:497-499
16. Consortium F, the R P, Clst, Forrest A R, Kawaji H, Rehli M, Baillie J K, de Hoon M J, Lassmann T, Itoh M, Summers K M, Suzuki H, Daub C O, Kawai J, Heutink P, Hide W, Freeman T C, Lenhard B, Bajic V B, Taylor M S, Makeev V J, Sandelin A, Hume D A, Carninci P, Hayashizaki Y. A promoter-level mammalian expression atlas. Nature 2014; 507:462-470
17. Le Hir H, Nott A, Moore M J. How introns influence and enhance eukaryotic gene expression. Trends in biochemical sciences 2003; 28:215-220
18. West A G, Gaszner M, Felsenfeld G. Insulators: many functions, many mechanisms. Genes & development 2002; 16:271-288
19. Edwards C A, Ferguson-Smith A C. Mechanisms regulating imprinted genes in clusters. Curr Opin Cell Biol 2007; 19:281-289
20. Toyoda N, Zavacki A M, Maia A L, Harney J W, Larsen P R. A novel retinoid X receptor-independent thyroid hormone response element is present in the human type 1 deiodinase gene. Molecular and cellular biology 1995; 15:5100-5112
21. Ivics Z, Mates L, Yau T Y, Landa V, Zidek V, Bashir S, Hoffmann O I, Hiripi L, Garrels W, Kues W A, Bosze Z, Geurts A, Pravenec M, Rulicke T, Izsvak Z. Germline transgenesis in rodents by pronuclear microinjection of Sleeping Beauty transposons. Nature protocols 2014; 9:773-793
22. Refetoff S, DeWind L T, DeGroot U. Familial syndrome combining deaf-mutism, stuppled epiphyses, goiter and abnormally high PBI: possible target organ refractoriness to thyroid hormone. The Journal of clinical endocrinology and metabolism 1967; 27:279-294
23. Ortiga-Carvalho T M, Sidhaye A R, Wondisford F E. Thyroid hormone receptors and resistance to thyroid hormone disorders. Nature reviews Endocrinology 2014; 10:582-591
24. Friesema E C, Grueters A, Biebermann H, Krude H, von Moers A, Reeser M, Barrett T G, Mancilla E E, Svensson J, Kester M H, Kuiper G G, Balkassmi S, Uitterlinden A G, Koehrle J, Rodien P, Halestrap A P, Visser T J. Association between mutations in a thyroid hormone transporter and severe X-linked psychomotor retardation. Lancet 2004; 364:1435-1437
25. Dumitrescu A M, Liao X H, Best T B, Brockmann K, Refetoff S. A novel syndrome combining thyroid and neurological abnormalities is associated with mutations in a monocarboxylate transporter gene. Am J Hum Genet 2004; 74:168-175
26. Boelen A, Kwakkel J, Fliers E. Beyond low plasma T3: local thyroid hormone metabolism during inflammation and infection. Endocrine reviews 2011; 32:670-693
27. Gereben B, McAninch E A, Ribeiro M O, Bianco A C. Scope and limitations of iodothyronine deiodinases in hypothyroidism. Nature reviews Endocrinology 2015; 11:642-652
28. Fonseca T L, Fernandes G W, McAninch E A, Bocco B M, Abdalla S M, Ribeiro M O, Mohacsik P, Fekete C, Li D, Xing X, Wang T, Gereben B, Bianco A C. Perinatal deiodinase 2 expression in hepatocytes defines epigenetic susceptibility to liver steatosis and obesity. Proceedings of the National Academy of Sciences of the United States of America 2015;
29. Kakucska I, Romero L I, Clark B D, Rondeel J M, Qi Y, Alex S, Emerson C H, Lechan R M. Suppression of thyrotropin-releasing hormone gene expression by interleukin-1-beta in the rat: implications for nonthyroidal illness. Neuroendocrinology 1994; 59:129-137
30. Silva J E, Larsen P R. Adrenergic activation of triiodothyronine production in brown adipose tissue. Nature 1983; 305:712-713
31. Curcio-Morelli C, Zavacki A M, Christofollete M, Gereben B, de Freitas B C, Harney J W, Li Z, Wu G, Bianco A C. Deubiquitination of type 2 iodothyronine deiodinase by von Hippel-Lindau protein-interacting deubiquitinating enzymes regulates thyroid hormone activation. The Journal of clinical investigation 2003; 112:189-196
32. Vaughan C H, Zarebidaki E, Ehlen J C, Bartness T J. Analysis and measurement of the sympathetic and sensory innervation of white and brown adipose tissue. Methods in enzymology 2014; 537:199-225
33. Bianco A C, Anderson G, Forrest D, Galton V A, Gereben B, Kim B W, Kopp P A, Liao X H, Obregon M J, Peeters R P, Refetoff S, Sharlin D S, Simonides W S, Weiss R E, Williams G R. American thyroid association guide to investigating thyroid hormone economy and action in rodent and cell models. Thyroid: official journal of the American Thyroid Association 2014; 24:88-168
34. Zeold A, Doleschall M, Haffner M C, Capelo L P, Menyhert J, Liposits Z, da Silva W S, Bianco A C, Kacskovics I, Fekete C, Gereben B. Characterization of the nuclear factor-kappa B responsiveness of the human dio2 gene. Endocrinology 2006; 147:4419-4429
35. Borngraeber S, Budny M J, Chiellini G, Cunha-Lima S T, Togashi M, Webb P, Baxter J D, Scanlan T S, Fletterick R J. Ligand selectivity by seeking hydrophobicity in thyroid hormone receptor. Proceedings of the National Academy of Sciences of the United States of America 2003; 100:15358-15363
36. Egri P, Gereben B. Minimal requirements for ubiquitination-mediated regulation of thyroid hormone activation. Journal of molecular endocrinology 2014; 53:217-226

The invention claimed is:

1. A thyroid hormone action indicator transgenic mouse, comprising stably integrated in its haploid genome a single copy of a recombinant DNA construct, useful for the assessment of thyroid hormone (TH) action, wherein the recombinant DNA construct comprises, in 5' to 3' direction, at least the following elements:
   a thyroid hormone responsive segment, wherein the thyroid hormone responsive segment comprises 1 to 5 copies of a thyroid hormone responsive element (TRE),
   a ubiquitous minimal promoter operably linked to an expression enhancer,
   a coding sequence encoding a reporter,
wherein the recombinant DNA construct is free of a sequence encoding a thyroid hormone receptor and
   the reporter is expressed at least in cells of one or more tissue(s) of said mouse selected from the group consisting of pituitary, hypothalamus, hippocampus, cortex, cerebellum, heart, liver, brown adipose tissue, bone, muscle, intestine and skin, and
   expression of the reporter is upregulated via the thyroid hormone responsive segment by a complex of a thyroid hormone receptor (TR) and a TH;
wherein the recombinant DNA construct is flanked by insulator sequences to protect the recombinant DNA construct from influences from neighboring sequences,
and wherein the recombinant DNA construct is integrated into the genome of the mouse using a transposon based delivery system or the recombinant DNA construct is present in the genome of the mouse due to genetic inheritance from a forebear into whose genome the recombinant DNA construct was integrated using a transposon based delivery system.

2. The transgenic mouse of claim 1, wherein the TRE is a TRE of the human dio1 gene.

3. The transgenic mouse of claim 1, wherein the reporter is a protein which, when expressed in a cell, said cell provides an optically detectable signal or which can be detected by an enzymatic assay or whose mRNA can be detected.

4. The transgenic mouse of claim 1, wherein said construct also comprises a resistance marker.

5. The transgenic mouse of claim 4, wherein the resistance marker is a positive resistance marker and/or the expression of the resistance marker is operably linked with the expression of the reporter.

6. The transgenic mouse of claim 1, wherein the thyroid hormone responsive segment comprises 3 copies of a thyroid hormone responsive element (TRE).

7. The transgenic mouse of claim 1, wherein the thyroid hormone responsive segment contains one or more thyroid hormone responsive element(s) (TRE) having the sequence motif of GGGTCA nnnn AGGTCA, the promoter is a thymidine kinase minimal promoter, the expression enhancer is in the form of an expression enhancer cassette.

8. The transgenic mouse of claim 7, wherein the thyroid hormone responsive segment contains a TRE of the 5' flanking region of a dio1 gene, the promoter is the thymidine kinase minimal promoter of the Herpes simplex virus, the expression enhancer cassette contains an intronic sequence.

9. The transgenic mouse of claim 1, wherein the transposon based delivery system is the Sleeping Beauty system.

10. The transgenic mouse of claim 1, wherein
    the thyroid hormone responsive segment comprises 3 copies of a TRE of the human diol gene,
    the promoter is a thymidine kinase minimal promoter of the *Herpes simplex* virus,
    the expression enhancer is in the form of an expression enhancer cassette that contains the untranslated leader (exon 1)-HTLV-1 R- Synthetic Rabbit β-globin-based 3' intron-intron unit of the NTC8681 vector,
    the insulator is the H19, and
    the transposon is the Sleeping Beauty transposon.

11. A method for the production of the transgenic mouse of claim 1, comprising the steps of:
   a) introducing a recombinant DNA construct comprising, in 5' to 3' direction, at least the following elements:
   a thyroid hormone responsive segment, wherein the thyroid hormone responsive segment comprises 1 to 5 copies of a thyroid hormone responsive element (TRE),
   a ubiquitous minimal promoter operably linked to an expression enhancer,
   a coding sequence encoding a reporter,
wherein the recombinant DNA construct is free of a sequence encoding a thyroid hormone receptor and is flanked by insulator sequences to protect the recombinant DNA construct from influences from neighbouring sequences;
and a nucleic acid encoding a transposon into a fertilized mouse oocyte,
   b) selecting the transgenic mouse that comprises stably integrated in its haploid genome a single copy of the recombinant DNA construct, and in which the reporter is expressed at least in cells of one or more tissue(s) selected from the group consisting of pituitary, hypothalamus, hippocampus, cortex, cerebellum, heart, liver, brown adipose tissue, bone, muscle, intestine and skin; and expression of the reporter is upregulated via the thyroid hormone responsive segment by a complex of a TR and a TH.

12. The method according to claim 11, wherein the TRE is a TRE of the human dio1 gene.

13. The method according to claim 11, wherein the reporter is a protein which, when expressed in a cell, said cell provides an optically detectable signal or which can be detected by an enzymatic assay or whose mRNA can be detected.

14. The method according to claim 11, wherein said construct also comprises a resistance marker.

15. The method according to claim 11, wherein the resistance marker is a positive resistance marker and/or
   the expression of the resistance marker is operably linked with the expression of the reporter.

* * * * *